US012636363B2

(12) United States Patent
Arguello et al.

(10) Patent No.: US 12,636,363 B2
(45) Date of Patent: May 26, 2026

(54) ANTI-TRANSFERRIN RECEPTOR FUSION PROTEINS AND METHODS OF USE THEREOF

(71) Applicant: DENALI THERAPEUTICS INC., South San Francisco, CA (US)

(72) Inventors: Annie Arguello, San Francisco, CA (US); Tina Giese, South San Francisco, CA (US); Gunasekaran Kannan, Daly City, CA (US); Mihalis S. Kariolis, San Mateo, CA (US); Cathal S. Mahon, San Francisco, CA (US); Junhua Wang, Fremont, CA (US)

(73) Assignee: DENALI THERAPEUTICS INC., South San Francisco, CA (US)

( * ) Notice: Subject to any disclaimer, the term of this patent is extended or adjusted under 35 U.S.C. 154(b) by 0 days.

(21) Appl. No.: 19/304,112

(22) Filed: Aug. 19, 2025

(65) Prior Publication Data

US 2025/0387477 A1    Dec. 25, 2025

Related U.S. Application Data

(62) Division of application No. 18/276,823, filed as application No. PCT/US2022/016229 on Feb. 11, 2022.

(60) Provisional application No. 63/148,543, filed on Feb. 11, 2021.

(51) Int. Cl.

| | |
|---|---|
| *A61K 39/395* | (2006.01) |
| *A61K 38/46* | (2006.01) |
| *A61P 3/00* | (2006.01) |
| *C07K 16/28* | (2006.01) |
| *C12N 9/16* | (2006.01) |
| *A61K 39/00* | (2006.01) |

(52) U.S. Cl.
CPC ........ A61K 39/3955 (2013.01); A61K 38/465 (2013.01); A61P 3/00 (2018.01); C07K 16/2881 (2013.01); C12N 9/16 (2013.01); C12Y 301/06013 (2013.01); A61K 2039/545 (2013.01); C07K 2319/30 (2013.01)

(58) Field of Classification Search
CPC .............. A61K 39/3955; A61K 38/465; A61K 2039/545; A61P 3/00; C07K 16/2881; C07K 2319/30; C12N 9/16; C12Y 301/06013
See application file for complete search history.

(56) References Cited

U.S. PATENT DOCUMENTS

| | | |
|---|---|---|
| 2016/0369001 A1 | 12/2016 | Sonoda et al. |
| 2018/0171012 A1 | 6/2018 | Sonoda et al. |
| 2019/0225700 A1 | 7/2019 | Koshimura et al. |
| 2019/0336586 A1 | 11/2019 | Yasukawa et al. |
| 2019/0338043 A1 | 11/2019 | Sonoda et al. |
| 2024/0148866 A1 | 5/2024 | Arguello et al. |

FOREIGN PATENT DOCUMENTS

| | | | | | |
|---|---|---|---|---|---|
| WO | WO-03032913 A2 | * | 4/2003 | ................ | A61P 9/10 |
| WO | 2013009526 A1 | | 1/2013 | | |
| WO | WO-2018038243 A1 | * | 3/2018 | ........... | C12N 9/2462 |
| WO | 2019070577 A1 | | 4/2019 | | |
| WO | 2020132452 A1 | | 6/2020 | | |

OTHER PUBLICATIONS

Finke et al. (BBA—General Subjects, 1861: 2228-2239, 2018).*
"Report on the Deliberation Results", Pharmaceutical Evaluation Division, Pharmaceutical Safety and Environmental Health Bureau, Ministry of Health, Labour and Welfare, 120 pages (Mar. 2021).
Giugliani, et al., "Iduronate-2-sulfatase fused with anti-hTfR antibody, pabinafusp alfa, for MPS-II: A phase 2 trial in Brazil", Molecular Therapy 29(7), 2378-2386 (Jul. 2021 in issue; Epub Mar. 2021).
Johnsen, et al., "Targeting the transferrin receptor for brain drug delivery", Progress in Neurobiology 181, 101665, 1-30 (2019).
Liu, L, "Antibody Glycosylation and Its Impact on the Pharmacokinetics and Pharmacodynamics of Monoclonal Antibodies and Fc-Fusion Proteins", Journal of Pharmaceutical Sciences 104, 1866-1884 (2015).
Morimoto, et al., "Clearance of heparan sulfate in the brain prevents neurodegeneration and neurocognitive impairment in MPS II mice", Molecular Therapy 29(5), 1853-1861 (May 2021 in issue; Epub Jan. 2021).
Okuyama, et al., "A Phase 2/3 Trial of Pabinafusp Alfa, IDS Fused with Anti-Human Transferrin Receptor Antibody, Targeting Neurodegeneration in MPS-II", Molecular Therapy 29 (2), 671-679 (Feb. 2021 in issue; Epub Sep. 2020).
Okuyama, et al., "Iduronate-2-Sulfatase with Anti-human Transferrin Receptor Antibody for Neuropathic Mucopolysaccharidosis II: A Phase 1/2 Trial", Molecular Therapy 27 (2), 456-464 (Feb. 2019 in issue; Epub Dec. 2018).
Patent Cooperation Treaty, International Search Report and Written Opinion for PCT/US2022016229, 20 pages dated Jun. 8, 2022.
Safary, et al., "Targeted enzyme delivery systems in lysosomal disorders: an innovative form of therapy for mucopolysaccharidosis", Cellular and Molecular Life Sciences 76, 3363-3381 (2019).
Sonoda, et al., "A blood-brain barrier-penetrating anti-human transferrin receptor antibody fusion protein for neuronopathic mucopolysaccharidosis II", Molecular Therapy 26(5), 1366-1374 (2018).
Tanaka, et al., "Evaluation of cerebrospinal fluid heparan sulfate as a biomarker of neuropathology in a murine model of mucopolysaccharidosis type II using high-sensitivity LC/MS/MS", Molecular Genetics and Metabolism 125, 53-58 (2018).

(Continued)

*Primary Examiner* — Nelson B Moseley, II
(74) *Attorney, Agent, or Firm* — Viksnins Harris Padys Malen LLP

(57) ABSTRACT

Certain embodiments provide a fusion protein comprising an iduronate 2-sulfatase (IDS) amino acid sequence, an IDS variant amino acid sequence, or a catalytically active fragment thereof; and an anti-transferrin receptor (TfR) antibody as described herein, as well as methods of use thereof.

19 Claims, 9 Drawing Sheets

Specification includes a Sequence Listing.

(56) References Cited

OTHER PUBLICATIONS

Ullman, et al., "Brain delivery and activity of a lysosomal enzyme using a blood-brain barrier transport vehicle in mice", Sci Transl Med 12, eaay1163, 13 pages (2020).

Bork, et al., "Increasing the Sialylation of Therapeutic Glycoproteins: The Potential of the Sialic Acid Biosynthetic Pathway", Journal of Pharmaceutical Sciences 98 (10), 3499-3508 (2009).

Chia, et al., "Enhancing pharmacokinetic and pharmacodynamic properties of recombinant therapeutic proteins by manipulation of sialic acid content", Biomedicine & Pharmacotherapy 163 (114757), 1-11 (2023).

Scallon, et al., "Higher levels of sialylated Fc glycans in immunoglobulin G molecules can adversely impact functionallity", Molecular Immunology 44, 1524-1534 (2007 in issue; Epub 2006).

Vattepu, et al., "Sialylation as an Important Regulator of Antibody Function", Front Immunol 13, 818736, 15 pages (2022).

* cited by examiner

IgG:IDS Fusion Protein

FIGURE 2

CSF GAGs

CSF HS

CSF DS

Brain GAGs

ANTI-TRANSFERRIN RECEPTOR FUSION PROTEINS AND METHODS OF USE THEREOF

CROSS REFERENCE TO RELATED APPLICATION

This application is a divisional of U.S. application Ser. No. 18/276,823, which is a 35 U.S.C. § 371 application of International Application Serial No. PCT/US2022/016229, filed on 11 Feb. 2022, which claims priority to U.S. Provisional Application Ser. No. 63/148,543, filed on 11 Feb. 2021. The entire content of the applications referenced above are hereby incorporated by reference herein.

SEQUENCE LISTING

The instant application contains a Sequence Listing which has been submitted electronically in XML format and is hereby incorporated by reference in its entirety. Said XML copy, created on Aug. 15, 2025, is named 02900_030US2_SL.xml and is 37,365 bytes in size.

BACKGROUND

Hunter syndrome, or MPS II, is a rare, X-linked recessive disorder caused by IDS gene mutations. Insufficient iduronate 2-sulfatase (IDS) activity leads to accumulation of the glycosaminoglycans (GAGs) heparan sulfate (HS) and dermatan sulfate (DS) and to lysosomal dysfunction in multiple organs and tissues. Approximately two-thirds of patients display a neuronopathic phenotype (nMPS II). A recombinant form of IDS has been approved to treat Hunter syndrome, but it has little effect on the brain due to difficulties in delivering the recombinant enzyme across the blood-brain barrier (BBB). One possible approach involves techniques that utilize an anti-transferrin receptor antibody to facilitate passage of large molecules, such as IDS, across the BBB.

SUMMARY

Accordingly, certain embodiments provide a fusion protein comprising:

(a) an iduronate 2-sulfatase (IDS) amino acid sequence, an IDS variant amino acid sequence, or a catalytically active fragment thereof, and (b) an anti-transferrin receptor (TfR) antibody as described herein (e.g., an anti-human TfR antibody), wherein the fusion protein comprises at least about 6 mol/mol sialic acid:fusion protein and/or comprises from about 1.5 to about 2.5 mol/mol mannose-6-phospate (M6P):fusion protein. In certain embodiments, the fusion protein comprises between about 15-16 mol/mol sialic acid:fusion protein (i.e., from about 15 to about 16 mol/mol sialic acid:fusion protein) and/or comprises between about 1.5 to about 2.5 mol/mol M6P:fusion protein (i.e., from about 1.5 to about 2.5 mol/mol M6P:fusion protein). In certain embodiments, the fusion protein comprises between about 15-16 mol/mol sialic acid:fusion protein (i.e., from about 15 to about 16 mol/mol sialic acid:fusion protein) and/or comprises between about 1.5 to about 2.3 mol/mol M6P:fusion protein (i.e., from about 1.5 to about 2.3 mol/mol M6P:fusion protein).

In certain embodiments, the fusion protein comprises:

(a) an iduronate 2-sulfatase (IDS) amino acid sequence, an IDS variant amino acid sequence, or a catalytically active fragment thereof, and (b) an anti-human transferrin receptor antibody, wherein the antibody comprises:

i) a heavy chain complementarity determining region 1 (CDR-H1) comprising GYSFTNY (SEQ ID NO:13), or a sequence having 1 or 2 substitutions relative to SEQ ID NO:13;

ii) a heavy chain CDR-H2 comprising YPGGDY (SEQ ID NO:15), or a sequence having 1 or 2 substitutions relative to SEQ ID NO: 15;

iii) a heavy chain CDR-H3 comprising SGNYDEVAY (SEQ ID NO:16), or a sequence having 1 or 2 substitutions relative to SEQ ID NO: 16;

iv) a light chain CDR-L1 comprising or RSSQSLVHSNGNTYLH (SEQ ID NO:7), or a sequence having 1 or 2 substitutions relative to SEQ ID NO:7;

v) a light chain CDR-L2 comprising KVSNRFS (SEQ ID NO:8), or a sequence having 1 or 2 substitutions relative to SEQ ID NO:8; and vi) a light chain CDR-L3 comprising SQSTHVPWT (SEQ ID NO:9), or a sequence having 1 or 2 substitutions relative to SEQ ID NO:9;

wherein the fusion protein comprises at least about 6 mol/mol sialic acid:fusion protein (e.g., between about 15-16 mol/mol sialic acid:fusion protein (i.e., from about 15 to about 16 mol/mol sialic acid:fusion protein)).

In certain other embodiments, the fusion protein comprises:

(a) an iduronate 2-sulfatase (IDS) amino acid sequence, an IDS variant amino acid sequence, or a catalytically active fragment thereof, and (b) an anti-human transferrin receptor antibody, wherein the antibody comprises:

i) a heavy chain CDR-H1 comprising GYSFTNY (SEQ ID NO:13), or a sequence having 1 or 2 substitutions relative to SEQ ID NO: 13;

ii) a heavy chain CDR-H2 comprising YPGGDY (SEQ ID NO:15), or a sequence having 1 or 2 substitutions relative to SEQ ID NO: 15;

iii) a heavy chain CDR-H3 comprising SGNYDEVAY (SEQ ID NO:16), or a sequence having 1 or 2 substitutions relative to SEQ ID NO: 16;

iv) a light chain CDR-L1 comprising RSSQSLVHSNGNTYLH (SEQ ID NO:7), or a sequence having 1 or 2 substitutions relative to SEQ ID NO:7;

v) a light chain CDR-L2 comprising KVSNRFS (SEQ ID NO:8), or a sequence having 1 or 2 substitutions relative to SEQ ID NO:8; and vi) a light chain CDR-L3 comprising SQSTHVPWT (SEQ ID NO:9), or a sequence having 1 or 2 substitutions relative to SEQ ID NO:9;

wherein the fusion protein comprises from about 1.5 to about 2.5 mol/mol M6P:fusion protein. In certain embodiments, the fusion protein comprises between about 1.5 to about 2.3 mol/mol M6P:fusion protein (i.e., from about 1.5 to about 2.3 mol/mol M6P:fusion protein).

Certain embodiments also provide a pharmaceutical composition comprising a fusion protein as described herein and a pharmaceutically acceptable excipient.

Certain embodiments provide a host cell comprising a fusion protein as described herein.

Certain embodiments provide method for producing a fusion protein as described herein, comprising expressing one or more polynucleotides operable to express 1) a light chain as described herein; and 2) a heavy chain linked to an IDS amino acid sequence as described herein, in a host cell under conditions suitable for producing the fusion protein.

Certain embodiments provide a fusion protein produced by a method as described herein.

Certain embodiments provide a method of reducing levels of one or more GAG species in a subject in need thereof, comprising administering a fusion protein as described herein or a pharmaceutical composition as described herein (e.g., administering a therapeutically effective dose as described herein) to the subject.

Certain embodiments provide a method of treating Hunter syndrome in a subject in need thereof, comprising administering a fusion protein as described herein or a pharmaceutical composition as described herein (e.g., administering a therapeutically effective dose as described herein) to the subject.

Certain embodiments also provide a method of reducing levels of one or more GAG species in a subject in need thereof, comprising administering to the subject a fusion protein at a dose of about 1 mg/kg, 3 mg/kg or 10 mg/kg, wherein the fusion protein comprises:

(a) an iduronate 2-sulfatase (IDS) amino acid sequence, an IDS variant amino acid sequence, or a catalytically active fragment thereof, and (b) an anti-human transferrin receptor antibody, wherein the antibody comprises:

i) a heavy chain complementarity determining region 1 (CDR-H1) comprising GYSFTNY (SEQ ID NO:13), or a sequence having 1 or 2 substitutions relative to SEQ ID NO:13;

ii) a heavy chain CDR-H2 comprising YPGGDY (SEQ ID NO:15), or a sequence having 1 or 2 substitutions relative to SEQ ID NO: 15;

iii) a heavy chain CDR-H3 comprising SGNYDEVAY (SEQ ID NO:16), or a sequence having 1 or 2 substitutions relative to SEQ ID NO: 16;

iv) a light chain CDR-L1 comprising RSSQSLVHSNGNTYLH (SEQ ID NO:7), or a sequence having 1 or 2 substitutions relative to SEQ ID NO:7;

v) a light chain CDR-L2 comprising KVSNRFS (SEQ ID NO:8), or a sequence having 1 or 2 substitutions relative to SEQ ID NO:8; and vi) a light chain CDR-L3 comprising SQSTHVPWT (SEQ ID NO:9), or a sequence having 1 or 2 substitutions relative to SEQ ID NO:9.

Certain embodiments provide a method of treating Hunter syndrome in a subject in need thereof, comprising administering to the subject a fusion protein at a dose of about 1 mg/kg, 3 mg/kg or 10 mg/kg, wherein the fusion protein comprises:

(a) an iduronate 2-sulfatase (IDS) amino acid sequence, an IDS variant amino acid sequence, or a catalytically active fragment thereof, and (b) an anti-human transferrin receptor antibody, wherein the antibody comprises:

i) a heavy chain complementarity determining region 1 (CDR-H1) comprising GYSFTNY (SEQ ID NO:13), or a sequence having 1 or 2 substitutions relative to SEQ ID NO:13;

ii) a heavy chain CDR-H2 comprising YPGGDY (SEQ ID NO:15), or a sequence having 1 or 2 substitutions relative to SEQ ID NO: 15;

iii) a heavy chain CDR-H3 comprising SGNYDEVAY (SEQ ID NO:16), or a sequence having 1 or 2 substitutions relative to SEQ ID NO: 16;

iv) a light chain CDR-L1 comprising RSSQSLVHSNGNTYLH (SEQ ID NO:7), or a sequence having 1 or 2 substitutions relative to SEQ ID NO:7;

v) a light chain CDR-L2 comprising KVSNRFS (SEQ ID NO:8), or a sequence having 1 or 2 substitutions relative to SEQ ID NO:8; and vi) a light chain CDR-L3 comprising SQSTHVPWT (SEQ ID NO:9), or a sequence having 1 or 2 substitutions relative to SEQ ID NO:9.

Certain embodiments also provide processes and intermediates disclosed herein that are useful for preparing a fusion protein as described herein.

BRIEF DESCRIPTION OF THE FIGURES

FIG. 2 shows IgG:IDS binding to the mannose-6-phosphate receptor (M6PR). An ELISA binding assay was performed using varying concentrations of IgG:IDS to generate the representative binding curve.

DETAILED DESCRIPTION

Figure 1:
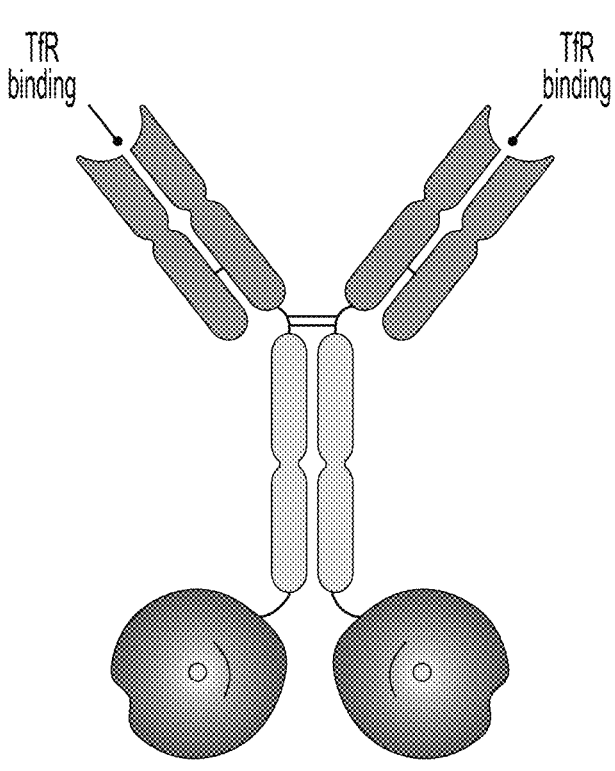
FIG. 1 is a schematic of the IgG:IDS fusion protein, which contains an anti-transferrin receptor antibody, wherein each heavy chain is fused to an IDS enzyme.

Hunter syndrome, specifically the neurocognitive phenotype, remains a significant unmet medical need. Described herein is the evaluation of a specific enzyme replacement therapy termed IgG:IDS, which is a fusion protein comprising an IDS enzyme amino acid sequence having the capability of crossing the BBB and treating certain CNS manifestations of Hunter syndrome. As described in the Examples, production of IgG:IDS results in specific posttranslational modifications (PTMs) of the fusion protein, including sialic acid and mannose 6-phosphate (M6P) modifications. These PTMs can impact peripheral (e.g. serum) exposure to the fusion protein and facilitate proper trafficking of the fusion protein to specific cells within the CNS, as well as sub-cellular trafficking. Further, the therapeutic response to IgG:IDS may be evaluated by measuring levels of glycosaminoglycan (GAG) species present in physiological samples from a subject. These levels may be used to identify and evaluate therapeutically effective doses of IgG: IDS.

Fusion Proteins

Accordingly, certain embodiments provide a fusion protein comprising:

(a) an iduronate 2-sulfatase (IDS) amino acid sequence, an IDS variant amino acid sequence, or a catalytically active fragment thereof, and (b) an anti-transferrin receptor (TfR) antibody as described herein (e.g., an anti-human TfR antibody). As described herein, such fusion proteins may comprise certain PTMs, including a particular molecular amount or range of amounts of certain PTMs, such as sialic acid and/or M6P (e.g., in an amount or range described herein).

In certain embodiments, the anti-TfR antibody specifically binds to TfR. In some embodiments, an antibody that specifically binds to human TfR exhibits cross-reactivity with one or more proteins of another species that correspond with human TfR (i.e., an TfR ortholog).

For example, in some embodiments, an anti-TfR antibody specifically binds to an epitope on TfR that is conserved among species, (e.g., structurally conserved among species), e.g., conserved between non-human primate and human species (e.g., structurally conserved between non-human primate and human species). In some embodiments, an anti-TfR receptor antibody may bind exclusively to a human TfR.

In some embodiments, an anti-TfR antibody is an anti-human TfR antibody. In some embodiments, an anti-human TfR antibody comprises one or more complementarity determining region (CDR) sequences as described herein. In certain embodiments, an anti-human TfR antibody comprises (1) a heavy chain variable region sequence, a heavy chain sequence, or fusion polypeptide comprising a heavy chain and an IDS amino acid sequence; and/or (2) a light chain variable region sequence or a light chain sequence, as described herein. For example, Table 6 shows the SEQ ID NOs of the respective amino acid sequences contained in CDR1 to CDR3 of the light chain variable region and CDR1 to CDR3 of the heavy chain variable region of an anti-hTfR antibody comprised within IgG:IDS (see, Example 1). However, Table 6 shows those amino acid sequences only as examples and does not limit the amino acid sequence of each CDR to those in Table 6. Rather, they can also either be regions of amino acid sequences that include any of these enumerated sequences, or amino acid sequences consisting of not less than three consecutive amino acids containing part of these sequences.

Thus, in certain embodiments, an anti-human TfR antibody comprises:

a) a heavy chain complementarity determining region 1 (CDR-H1) comprising GYSFX$_1$NY (SEQ ID NO: 12); or an amino acid sequence having 1 or 2 substitutions relative to SEQ ID NO:12, wherein X$_1$ is M or T;

b) a heavy chain CDR-H2 comprising YPGGDY (SEQ ID NO:15); or an amino acid sequence having 1 or 2 substitutions relative to SEQ ID NO: 15;

c) a heavy chain CDR-H3 comprising SGNYDEVAY (SEQ ID NO:16), or an amino acid sequence having 1 or 2 substitutions relative to SEQ ID NO: 16;

d) a light chain CDR-L1 comprising RSSQSLVHSNGN-TYLH (SEQ ID NO:7), or an amino acid sequence having 1 or 2 substitutions relative to SEQ ID NO:7;

e) a light chain CDR-L2 comprising KVSNRFS (SEQ ID NO:8), or an amino acid sequence having 1 or 2 substitutions relative to SEQ ID NO: 8; and f) a light chain CDR-L3 comprising SQSTHVPWT (SEQ ID NO:9), or an amino acid sequence having 1 or 2 substitutions relative to SEQ ID NO:9.

In some embodiments, a CDR has one amino acid substitution relative to the reference sequence. In some embodiments, a CDR has two amino acid substitutions relative to the reference sequence. In some embodiments, the amino acid substitution(s) are conservative substitutions.

Thus, in some embodiments, an anti-human TfR antibody comprises:

a) a heavy chain CDR-H1 comprising GYSFX$_1$NY (SEQ ID NO: 12); or an amino acid sequence having 1 substitution relative to SEQ ID NO: 12, wherein X$_1$ is M or T;

b) a heavy chain CDR-H2 comprising YPGGDY (SEQ ID NO:15); or an amino acid sequence having 1 substitution relative to SEQ ID NO: 15;

c) a heavy chain CDR-H3 comprising SGNYDEVAY (SEQ ID NO:16), or an amino acid sequence having 1 substitution relative to SEQ ID NO:16;

d) a light chain CDR-L1 comprising RSSQSLVHSNGN-TYLH (SEQ ID NO:7), or an amino acid sequence having 1 substitution relative to SEQ ID NO:7;

e) a light chain CDR-L2 comprising KVSNRFS (SEQ ID NO:8), or an amino acid sequence having 1 substitution relative to SEQ ID NO:8; and f) a light chain CDR-L3 comprising SQSTHVPWT (SEQ ID NO:9), or an amino acid sequence having 1 substitution relative to SEQ ID NO:9.

In some embodiments, an anti-human TfR antibody comprises: a heavy chain CDR-H1 comprising GYSFX$_1$NY (SEQ ID NO: 12), wherein X$_1$ is M or T; a heavy chain CDR-H2 comprising YPGGDY (SEQ ID NO:15); a heavy chain CDR-H3 comprising SGNYDEVAY (SEQ ID NO:16); a light chain CDR-L1 comprising RSSQSLVHSNGNTYLH (SEQ ID NO:7); a light chain CDR-L2 comprising KVSNRFS (SEQ ID NO:8); and a light chain CDR-L3 comprising SQSTHVPWT (SEQ ID NO:9).

In some embodiments, an anti-human TfR antibody comprises: a heavy chain CDR-H1 consisting of GYSFX$_1$NY (SEQ ID NO: 12), wherein X$_1$ is M or T; a heavy chain CDR-H2 consisting of YPGGDY (SEQ ID NO:15); a heavy chain CDR-H3 consisting of SGNYDEVAY (SEQ ID NO:16); a light chain CDR-L1 consisting of RSSQSLVHSNGNTYLH (SEQ ID NO:7); a light chain CDR-L2 consisting of KVSNRFS (SEQ ID NO:8); and a light chain CDR-L3 consisting of SQSTHVPWT (SEQ ID NO:9).

In some embodiments, an anti-human TfR antibody comprises: a heavy chain CDR-H1 comprising GYSFTNY (SEQ ID NO: 13); a heavy chain CDR-H2 comprising YPGGDY (SEQ ID NO:15); a heavy chain CDR-H3 comprising SGNYDEVAY (SEQ ID NO:16); a light chain CDR-L1 comprising RSSQSLVHSNGNTYLH (SEQ ID NO:7); a light chain CDR-L2 comprising KVSNRFS (SEQ ID NO:8); and a light chain CDR-L3 comprising SQSTHVPWT (SEQ ID NO:9).

In some embodiments, an anti-human TfR antibody comprises: a heavy chain CDR-H1 consisting of GYSFTNY (SEQ ID NO:13); a heavy chain CDR-H2 consisting of YPGGDY (SEQ ID NO:15); a heavy chain CDR-H3 consisting of SGNYDEVAY (SEQ ID NO:16); a light chain CDR-L1 consisting of RSSQSLVHSNGNTYLH (SEQ ID NO:7); a light chain CDR-L2 consisting of KVSNRFS (SEQ ID NO:8); and a light chain CDR-L3 consisting of SQSTHVPWT (SEQ ID NO:9).

In some embodiments, an anti-human TfR antibody comprises: a heavy chain CDR-H1 comprising GYSFMNY (SEQ ID NO:14); a heavy chain CDR-H2 comprising YPGGDY (SEQ ID NO:15); a heavy chain CDR-H3 comprising SGNYDEVAY (SEQ ID NO:16); a light chain CDR-L1 comprising RSSQSLVHSNGNTYLH (SEQ ID NO:7); a light chain CDR-L2 comprising KVSNRFS (SEQ ID NO:8); and a light chain CDR-L3 comprising SQSTHVPWT (SEQ ID NO:9).

In some embodiments, an anti-human TfR antibody comprises: a heavy chain CDR-H1 consisting of GYSFMNY (SEQ ID NO:14); a heavy chain CDR-H2 consisting of YPGGDY (SEQ ID NO:15); a heavy chain CDR-H3 consisting of SGNYDEVAY (SEQ ID NO:16); a light chain CDR-L1 consisting of RSSQSLVHSNGNTYLH (SEQ ID NO:7); a light chain CDR-L2 consisting of KVSNRFS (SEQ ID NO:8); and a light chain CDR-L3 consisting of SQSTHVPWT (SEQ ID NO:9).

In some embodiments, an anti-human TfR antibody comprises a light chain variable region comprising an amino acid sequence that has at least 90% sequence identity (e.g., at least 91%, at least 92%, at least 93%, at least 94%, at least 95%, at least 96%, at least 97%, at least 98%, at least 99% or 100% sequence identity) to:

```
                                    (SEQ ID NO: 6)
DIVMTQTPLSLSVTPGQPASISCRSSQSLVHSN

GNTYLHWYLQKPGQSPQLLIYKVSNRFSGVPDR

FSGSGSGTDFTLKISRVEAEDVGVYYCSQSTHV

PWTFGQGTKVEIK.
```

In some embodiments, a light chain variable region having at least 90% sequence identity to a SEQ ID NO:6 contains one, two, three, four, five, six, seven, eight, nine, ten or more substitutions (e.g., conservative substitutions) or insertions, but retains the ability to specifically bind to a TfR. In some embodiments, a light chain variable region contains one, two, or three substitutions (e.g., conservative substitutions) in SEQ ID NO:6.

In some embodiments, an anti-human TfR antibody comprises a light chain variable region comprising the amino acid sequence of SEQ ID NO:6.

In some embodiments, an anti-human TfR antibody comprises a light chain variable region consisting of the amino acid sequence of SEQ ID NO:6.

In some embodiments, an anti-human TfR antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, at least 99% or 100% sequence identity) to:

```
                                    (SEQ ID NO: 11)
EVQLVQSGAEVKKPGESLKISCKGSGYSFTNYWLGWVRQM

PGKGLEWMGDIYPGGDYPTYSEKFKVQVTISADKSISTAY

LQWSSLKASDTAMYYCARSGNYDEVAYWGQGTLVTVSS.
```

In some embodiments, a heavy chain variable region having at least 90% sequence identity to a SEQ ID NO:11 contains one, two, three, four, five, six, seven, eight, nine, ten or more substitutions (e.g., conservative substitutions) or insertions, but retains the ability to specifically bind to a TfR. In some embodiments, a heavy chain variable region contains one, two, or three substitutions (e.g., conservative substitutions) in SEQ ID NO:11.

In some embodiments, an anti-human TfR antibody comprises a heavy chain variable region comprising the amino acid sequence of SEQ ID NO:11.

In some embodiments, an anti-human TfR antibody comprises a heavy chain variable region consisting of the amino acid sequence of SEQ ID NO:11.

In some embodiments, an anti-human TfR antibody comprises a light chain variable region comprising an amino acid sequence that has at least 90% sequence identity (e.g., at least 91%, at least 92%, at least 93%, at least 94%, at least 95%, at least 96%, at least 97%, at least 98%, at least 99% or 100% sequence identity) to SEQ ID NO: 6 and further comprises a heavy chain variable region comprising an amino acid sequence that has at least 90% sequence identity (e.g., at least 91%, at least 92%, at least 93%, at least 94%, at least 95%, at least 96%, at least 97%, at least 98%, at least 99% or 100% sequence identity) to SEQ ID NO: 11.

In some embodiments, an anti-human TfR antibody comprises a light chain variable region comprising an amino acid sequence of SEQ ID NO: 6 and further comprises a heavy chain variable region comprising an amino acid sequence of SEQ ID NO: 11.

In some embodiments, an anti-human TfR antibody comprises a light chain variable region consisting of an amino acid sequence of SEQ ID NO: 6 and further comprises a heavy chain variable region consisting of an amino acid sequence of SEQ ID NO: 11.

As described herein, the anti-human TfR antibody may be a substantially full-length antibody, e.g., an IgG antibody, such as an $IgG_1$ antibody, or other antibody class or isotype as defined herein (e.g., a $IgG_2$, $IgG_3$ or $IgG_4$ antibody). Thus, in certain embodiments, the antibody comprises at least one heavy chain constant region and/or at least one light chain constant region (e.g., kappa or lambda).

In certain embodiments, the anti-human TfR antibody comprises a light chain constant region. In certain embodiments, an anti-human TfR antibody comprises a light chain comprising an amino acid sequence that has at least 90% sequence identity (e.g., at least 91%, at least 92%, at least 93%, at least 94%, at least 95%, at least 96%, at least 97%, at least 98%, at least 99% or 100% sequence identity) to:

```
                                      (SEQ ID NO: 5)
DIVMTQTPLSLSVTPGQPASISCRSSQSLVHSNGNTYLHW

YLQKPGQSPQLLIYKVSNRFSGVPDRFSGSGSGTDFTLKI

SRVEAEDVGVYYCSQSTHVPWTFGQGTKVEIKRTVAAPSV

FIFPPSDEQLKSGTASVVCLLNNFYPREAKVQWKVDNALQ

SGNSQESVTEQDSKDSTYSLSSTLTLSKADYEKHKVYACE

VTHQGLSSPVTKSFNRGEC.
```

In some embodiments, a light chain having at least 90% sequence identity to a SEQ ID NO:5 contains one, two, three, four, five, six, seven, eight, nine, ten or more substitutions (e.g., conservative substitutions) or insertions, but retains the ability to specifically bind to a TfR. In some embodiments, a light chain contains one, two, or three substitutions (e.g., conservative substitutions) in SEQ ID NO:5.

In some embodiments, an anti-human TfR antibody comprises a light chain comprising the amino acid sequence of SEQ ID NO:5.

In some embodiments, an anti-human TfR antibody comprises a light chain consisting of the amino acid sequence of SEQ ID NO:5.

In certain embodiments, an anti-human TfR antibody is an IgG$_1$ antibody comprising constant region(s) from IgG$_1$. For example, in certain embodiments, an anti-human TfR antibody comprises an IgG$_1$ Fc region (see, e.g., SEQ ID NO:24). Thus, in some embodiments, an anti-human TfR antibody comprises a heavy chain comprising an amino acid sequence that has at least 90% sequence identity (e.g., at least 91%, at least 92%, at least 93%, at least 94%, at least 95%, at least 96%, at least 97%, at least 98%, at least 99% or 100% sequence identity) to:

```
                                      (SEQ ID NO: 10)
EVQLVQSGAEVKKPGESLKISCKGSGYSFTNYWLGWVRQM

PGKGLEWMGDIYPGGDYPTYSEKFKVQVTISADKSISTAY

LQWSSLKASDTAMYYCARSGNYDEVAYWGQGTLVTVSSAS

TKGPSVFPLAPSSKSTSGGTAALGCLVKDYFPEPVTVSWN

SGALTSGVHTFPAVLQSSGLYSLSSVVTVPSSSLGTQTYI

CNVNHKPSNTKVDKKVEPKSCDKTHTCPPCPAPELLGGPS

VFLFPPKPKDTLMISRTPEVTCVVVDVSHEDPEVKFNWYV

DGVEVHNAKTKPREEQYNSTYRVVSVLTVLHQDWLNGKEY

KCKVSNKALPAPIEKTISKAKGQPREPQVYTLPPSRDELT

KNQVSLTCLVKGFYPSDIAVEWESNGQPENNYKTTPPVLD

SDGSFFLYSKLTVDKSRWQQGNVFSCSVMHEALHNHYTQK

SLSLSPGK.
```

In some embodiments, a heavy chain having at least 90% sequence identity to a SEQ ID NO:10 contains one, two, three, four, five, six, seven, eight, nine, ten or more substitutions (e.g., conservative substitutions) or insertions, but retains the ability to specifically bind to a TfR. In some embodiments, a heavy chain contains one, two, or three substitutions (e.g., conservative substitutions) in SEQ ID NO:10.

In some embodiments, an anti-human TfR antibody comprises a heavy chain comprising the amino acid sequence of SEQ ID NO:10.

In some embodiments, an anti-human TfR antibody comprises a heavy chain consisting of the amino acid sequence of SEQ ID NO:10.

In some embodiments, an anti-human TfR antibody comprises a light chain comprising an amino acid sequence that has at least 90% sequence identity (e.g., at least 91%, at least 92%, at least 93%, at least 94%, at least 95%, at least 96%, at least 97%, at least 98%, at least 99% or 100% sequence identity) to SEQ ID NO: 5 and further comprises a heavy chain comprising an amino acid sequence that has at least 90% sequence identity (e.g., at least 91%, at least 92%, at least 93%, at least 94%, at least 95%, at least 96%, at least 97%, at least 98%, at least 99% or 100% sequence identity) to SEQ ID NO: 10.

In some embodiments, an anti-human TfR antibody comprises a light chain comprising an amino acid sequence of SEQ ID NO: 5 and further comprises a heavy chain comprising an amino acid sequence of SEQ ID NO: 10.

In some embodiments, an anti-human TfR antibody comprises a light chain consisting of an amino acid sequence of SEQ ID NO: 5 and further comprises a heavy chain consisting of an amino acid sequence of SEQ ID NO: 10.

In certain embodiments, an iduronate 2-sulfatase (IDS) amino acid sequence, an IDS variant amino acid sequence, or a catalytically active fragment thereof, is linked directly or via a linker to the C-terminus of the antibody heavy chain (i.e., to generate a heavy chain fusion polypeptide).

In some embodiments, an IDS amino acid sequence (i.e., an IDS amino acid sequence, an IDS variant amino acid sequence, or a catalytically active fragment thereof) is linked to the C-terminus of the antibody heavy chain directly (e.g., by a peptide bond). In certain other embodiments, an IDS amino acid sequence is linked to the C-terminus of the antibody heavy chain by a linker, e.g., a peptide linker. The peptide linker may be configured such that it allows for the rotation of the IDS enzyme relative to the anti-hTfR antibody to which it is joined; and/or is resistant to digestion by proteases. Peptide linkers may contain natural amino acids, unnatural amino acids, or a combination thereof. In some embodiments, the peptide linker may be a flexible linker, e.g., containing amino acids such as Gly, Asn, Ser, Thr, Ala, and the like. Such linkers are designed using known parameters and may be of any length and contain any number of repeat units of any length (e.g., repeat units of Gly and Ser residues). In certain embodiments, the peptide linker is between 1-50 amino acids in length, 1-40 amino acids in length, 1-30 amino acids in length, 1-20 amino acids in length, 1-15 amino acids in length, 1-10 amino acids in length or 1-5 amino acids in length (e.g., 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids in length). In certain embodiments, the peptide linker is composed of glycine or serine, for example, one consisting of a single amino acid either glycine or serine, the amino acid sequence Gly-Ser, the amino acid sequence Gly-Gly-Ser, the amino acid sequence Gly-Gly-Gly-Gly-Ser (SEQ ID NO:19), the amino acid sequence Gly-Gly-Gly-Gly-Gly-Ser (SEQ ID NO:20), the amino acid sequence Ser-Gly-Gly-Gly-fly (SEQ ID NO:21), or a sequence which includes 1-10 or 2-5 (e.g. 2, 3, 4 or 5) of any of those amino acid sequences consecutively linked. In some embodiments, the peptide linker may include a protease cleavage site, e.g., that is cleavable by an enzyme present in the central nervous system.

In certain embodiments, an IDS amino acid sequence is linked to the C-terminus of the heavy chain by a peptide linker comprising an amino acid sequence selected from the group consisting of a single glycine residue, a single serine residue, GGGGS (SEQ ID NO: 19), GGGGGS (SEQ ID NO: 20), SGGGG (SEQ ID NO: 21), GGS, GS, and amino acid sequences consisting of 2 to 10 of any of the aforementioned sequences that are consecutively linked. In certain embodiments, the peptide linker consists of an amino acid sequence selected from the group consisting of a single glycine residue, a single serine residue, GGGGS (SEQ ID NO: 19), GGGGGS (SEQ ID NO: 20), SGGGG (SEQ ID NO: 21), GGS, GS, and amino acid sequences consisting of 2 to 10 of any of the aforementioned sequences that are consecutively linked.

In some embodiments, an IDS amino acid sequence is linked to the C-terminus of the heavy chain by a Gly-Ser linker.

Thus, in certain embodiments, a fusion protein described herein comprises an anti-human TfR antibody and an IDS amino acid sequence linked to the C-terminus of the heavy chain by a peptide linker (i.e., a heavy chain fusion polypeptide), which comprises, in order from N'terminus to C'terminus: a heavy chain (SEQ ID NO:10), a Gly-Ser linker, and an IDS amino acid sequence, an IDS variant amino acid sequence, or a catalytically active fragment thereof. In certain embodiments, a fusion protein comprises an anti-human TfR antibody comprising a light chain comprising an amino acid sequence of SEQ ID NO: 5; and a heavy chain linked to an IDS amino acid sequence, an IDS variant amino acid sequence, or a catalytically active fragment thereof, by a peptide linker, which comprises, in order from N'terminus to C'terminus: SEQ ID NO:10, a Gly-Ser linker, and an IDS amino acid sequence, an IDS variant amino acid sequence, or a catalytically active fragment thereof.

In certain embodiments, the IDS amino acid sequence is a wild-type IDS amino acid sequence, or is a catalytically active variant or fragment of a wild-type IDS, e.g., a wild-type human IDS. In some embodiments, a catalytically active variant or fragment of an IDS enzyme has at least 50%, at least 55%, at least 60%, at least 65%, at least 70%, at least 75%, at least 80%, at least 85%, at least 90%, at least 95%, or greater of the activity of the wild-type IDS enzyme.

In some embodiments, an IDS enzyme, or a catalytically active variant or fragment thereof, that is present in a fusion protein described herein, retains at least 25% of its activity compared to its activity when not joined to an anti-TfR antibody. In some embodiments, an IDS enzyme, or a catalytically active variant or fragment thereof, retains at least 10%, or at least 15%, 20%, 25%, 30%, 35%, 40%, 45%, 50%, 55%, 60%, 65%, 70%, 75%, 80%, 85%, 90%, or 95%, of its activity compared to its activity when not joined to an anti-TfR antibody. In some embodiments, an IDS enzyme, or a catalytically active variant or fragment thereof, retains at least 80%, 85%, 90%, or 95% of its activity compared to its activity when not joined to an anti-TfR antibody. In some embodiments, fusion to an anti-TfR antibody does not decrease the activity of the IDS enzyme, or catalytically active variant or fragment thereof. In some embodiments, fusion to an anti-TfR antibody does not decrease the activity of the IDS enzyme.

In certain embodiments, the IDS amino acid sequence comprises an amino acid sequence having at least about 80%, 85%, 90%, or 95% sequence identity to SEQ ID NO:1, 2, 3 or 4. In certain embodiments, the IDS amino acid sequence comprises an amino acid sequence having at least about 80%, 85%, 90%, 95%, 96%, 97%, 98%, or 99% sequence identity to SEQ ID NO:1, 2, 3 or 4. In certain embodiments, the IDS amino acid sequence comprises SEQ ID NO:1, 2, 3 or 4. In certain embodiments, the IDS amino acid sequence consists of SEQ ID NO:1, 2, 3 or 4.

In certain embodiments, the IDS amino acid sequence comprises SEQ ID NO: 3 or 4. In certain embodiments, the IDS amino acid sequence comprises SEQ ID NO: 3. In certain embodiments, the IDS amino acid sequence consists of SEQ ID NO: 3. In certain embodiments, the IDS amino acid sequence comprises SEQ ID NO: 4. In certain embodiments, the IDS amino acid sequence consists of SEQ ID NO: 4.

Thus, in certain embodiments, a fusion protein comprises an anti-human TfR antibody comprising heavy chain linked to an IDS amino acid sequence (i.e., a heavy chain fusion polypeptide), which comprises an amino acid sequence having at least about 80%, 85%, 90%, 95%, 96%, 97%, 98%, or 99% sequence identity to SEQ ID NO: 17 or 18. In certain embodiments, the heavy chain linked to an IDS amino acid sequence (i.e., a heavy chain fusion polypeptide) comprises an amino acid sequence having at least about 90% sequence identity to SEQ ID NO:17 or 18. In certain embodiments, the heavy chain linked to an IDS amino acid sequence comprises SEQ ID NO:17 or 18. In certain embodiments, the heavy chain linked to an IDS amino acid sequence consists of SEQ ID NO: 17 or 18.

In certain embodiments, a fusion protein comprises an anti-human TfR antibody comprising heavy chain linked to an IDS amino acid sequence (i.e., a heavy chain fusion polypeptide), which comprises an amino acid sequence having at least about 80%, 85%, 90%, 95%, 96%, 97%, 98%, or 99% sequence identity to SEQ ID NO: 17. In certain embodiments, the heavy chain linked to an IDS amino acid sequence comprises SEQ ID NO:17. In certain embodiments, the heavy chain linked to an IDS amino acid sequence consists of SEQ ID NO:17.

In certain embodiments, an anti-human TfR antibody comprises a light chain comprising an amino acid sequence of SEQ ID NO: 5; and a heavy chain linked to an IDS amino acid sequence comprising an amino acid sequence of SEQ ID NO: 17. In certain embodiments, an anti-human TfR antibody comprises a light chain consisting of SEQ ID NO: 5; and a heavy chain linked to an IDS amino acid sequence, which consists of SEQ ID NO:17.

In certain embodiments, a fusion protein comprises an anti-human TfR antibody comprising heavy chain linked to an IDS amino acid sequence (i.e., a heavy chain fusion polypeptide), which comprises an amino acid sequence having at least about 80%, 85%, 90%, 95%, 96%, 97%, 98%, or 99% sequence identity to SEQ ID NO: 18. In certain embodiments, the heavy chain linked to an IDS amino acid sequence comprises SEQ ID NO: 18. In certain embodiments, the heavy chain linked to an IDS amino acid sequence consists of SEQ ID NO:18.

In certain embodiments, an anti-human TfR antibody comprises a light chain comprising an amino acid sequence of SEQ ID NO: 5; and a heavy chain linked to an IDS amino acid sequence comprising an amino acid sequence of SEQ ID NO: 18. In certain embodiments, an anti-human TfR antibody comprises a light chain consisting of SEQ ID NO: 5; and a heavy chain linked to an IDS amino acid sequence, which consists of SEQ ID NO:18.

Certain embodiments provide a fusion protein as described herein.

In a further aspect, a fusion protein according to any of the above embodiments, or anti-human TfR antibody comprised therein, may incorporate any of the features as described below, singly or in combination.

Fc Region Variants

In certain embodiments, one or more amino acid modifications may be introduced into the Fc region of a fusion protein/antibody described herein, thereby generating an Fc region variant. The Fc region variant may comprise a human Fc region sequence (e.g., a human $IgG_1$, $IgG_2$, $IgG_3$ or $IgG_4$ Fc region) comprising an amino acid modification (e.g. a substitution) at one or more amino acid positions.

In certain embodiments, an antibody variant possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC include, NK cells, which express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci.* USA 83:7059-7063 (1986)) and Hellstrom, I et al., *Proc. Nat'l Acad. Sci.* USA 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (Cell Technology, Inc. Mountain View, CA; and Cyto-Tox 96® non-radioactive cytotoxicity assay (Promega, Madison, WI). Useful effector cells for such assays include peripheral blood mononuclear cells (PBMC) and Natural Killer (NK) cells.

Alternatively, or additionally, ADCC activity of the molecule of interest may be assessed in vivo, e.g., in an animal model such as that disclosed in Clynes et al. *Proc. Nat'l Acad. Sci.* USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments Pro329 of a wild-type human Fc region is substituted with glycine, arginine, serine, or an amino acid residue large enough to destroy the proline sandwich within the Fc/Fcγ receptor interface, that is formed between the proline 329 of the Fc and tryptophan residues Trp 87 and Trp 110 of FcγRIII (Sondermann et al.: Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human $IgG_1$ Fc region or S228P and L235E of the human $IgG_4$ Fc region (U.S. Pat. No. 8,969,526 which is incorporated by reference in its entirety).

In certain embodiments, a polypeptide comprises the Fc variant of a wild-type human IgG Fc region wherein the polypeptide has Pro329 of the human IgG Fc region substituted with glycine and wherein the Fc variant comprises at least two further amino acid substitutions at L234A and L235A of the human $IgG_1$ Fc region or S228P and L235E of the human $IgG_4$ Fc region, and wherein the residues are numbered according to the EU index of Kabat (U.S. Pat. No. 8,969,526 which is incorporated by reference in its entirety). In certain embodiments, the polypeptide comprising the P329G, L234A and L235A substitutions exhibit a reduced affinity to the human FcγRIIIA and FcγRIIA, for down-modulation of ADCC to at least 20% of the ADCC induced by the polypeptide comprising the wild type human IgG Fc region, and/or for down-modulation of ADCP (U.S. Pat. No. 8,969,526 which is incorporated by reference in its entirety).

In a specific embodiment the polypeptide comprising an Fc variant of a wild type human Fc polypeptide comprises a triple mutation: an amino acid substitution at position Pro329, a L234A and a L235A mutation (P329/LALA) (U.S. Pat. No. 8,969,526 which is incorporated by reference in its entirety). In some embodiments, the polypeptide comprises the following amino acid substitutions: P329G, L234A, and L235A. In some embodiments, the polypeptide comprises the following amino acid substitutions: P329S, L234A, and L235A.

Certain antibody variants with improved or diminished binding to FcRs are known in the art and described herein. (See, e.g., U.S. Pat. No. 6,737,056; WO 2004/056312, and Shields et al., (2001) J. Biol. Chem. 9(2): 6591-6604).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 1999/51642, and Idusogie et al., *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 1994/29351 concerning other examples of Fc region variants.

Post-Translational Modification: Sialic Acid and Mannose-6-Phosphate

Post-translational modification (PTM) is a biological process that involves the modification of an amino acid side chain, carboxyl group, or terminal amino, by covalent or enzymatic modification. Such modifications may include, e.g., glycosylation, sialylation, phosphorylation, or acetylation of one or more amino acids in the protein. The PTMs of a particular protein may not be able to be predicted based on sequence alone and can vary based on protein production and purification methods. PTMs have been shown to be important in determining protein function and stability. For example, heterogeneity of glycoforms may impact, e.g., antibody stability, pharmacokinetics (PK), efficacy, immunogenicity, and/or Fc receptor binding.

An IgG:IDS fusion protein as described herein comprises specific PTMs, including sialic acid and mannose 6-phosphate modifications. These PTMs facilitate proper trafficking of the fusion protein to specific cells within the CNS, as well as sub-cellular trafficking. In addition, the PTMs can impact exposure (e.g., pharmacokinetics) of the fusion protein in vivo. For example, the mannose-6-phosphate (M6P) glycan, which binds to the mannose-6-phosphate receptor (M6PR), has been shown to be involved in cellular uptake and lysosomal targeting.

Methods of evaluating the molecular amount of a particular modification present in a protein of interest, such as sialic acid or M6P, are known in the art. A non-limiting example of such an assay is described in Example 3, in which liquid chromatography-mass spectrometry analysis is used to determine the mol/mol of M6P:fusion protein and mol/mol of SA:fusion protein. Methods for examining M6PR binding/affinity are also known in the art. For example, a fluorometric enzymatic assay, as described in Example 2, may be used.

In certain embodiments, a fusion protein as described herein comprises at least about 6 mol/mol sialic acid:fusion protein. In certain embodiments, a fusion protein as described herein comprises at least about 8 mol/mol sialic acid:fusion protein. In certain embodiments, a fusion protein as described herein comprises at least about 10 mol/mol sialic acid:fusion protein. In certain embodiments, a fusion protein as described herein comprises at least about 12 mol/mol sialic acid:fusion protein. In certain embodiments, a fusion protein as described herein comprises at least about 14 mol/mol sialic acid:fusion protein. In certain embodiments, a fusion protein as described herein comprises at least about 15 mol/mol sialic acid:fusion protein. In certain embodiments, a fusion protein as described herein comprises between about 6 to about 19 mol/mol sialic acid:fusion protein (i.e., from about 6 to about 19 mol/mol sialic acid:fusion protein). In certain embodiments, a fusion protein as described herein comprises between about 6 to about 16 mol/mol sialic acid:fusion protein (i.e., from about 6 to about 16 mol/mol sialic acid:fusion protein). In some embodiments, a fusion protein described herein comprises about 6 mol/mol sialic acid:fusion protein. In certain embodiments, a fusion protein as described herein comprises between about 12 to about 19 mol/mol sialic acid:fusion protein (i.e., from about 12 to about 19 mol/mol sialic acid:fusion protein). In certain embodiments, a fusion protein as described herein comprises between about 15-16 mol/mol sialic acid:fusion protein (i.e., from about 15 to about 16 mol/mol sialic acid:fusion protein). In some embodiments, a fusion protein described herein comprises about 15 mol/mol sialic acid:fusion protein. In some embodiments, a fusion protein described herein comprises about 16 mol/mol sialic acid:fusion protein.

In certain embodiments, a fusion protein as described herein comprises between about 1.5 to about 2.5 mol/mol M6P:fusion protein (i.e., from about 1.5 to about 2.5 mol/mol M6P:fusion protein). In certain embodiments, a fusion protein as described herein comprises between about 1.5 to about 2.3 mol/mol M6P:fusion protein (i.e., from about 1.5 to about 2.3 mol/mol M6P:fusion protein). In some embodiments, a fusion protein described herein comprises about 1.5 mol/mol M6P:fusion protein. In some embodiments, a fusion protein described herein comprises about 1.7 mol/mol M6P:fusion protein. In some embodiments, a fusion protein described herein comprises about 2.3 mol/mol M6P:fusion protein.

Affinity, Binding Kinetics, Concentration/Exposure, and Functional Characterization Fusion proteins described herein may have a range of binding affinities. In some embodiments, a fusion protein has an affinity for a TfR, ranging anywhere from about 1 pM to 2500 pM. For example, in some embodiments, a fusion protein has an affinity for a TfR, ranging anywhere from about 1 pM to 500 pM. In some embodiments, the affinity for a TfR ranges from about 10 pM to 250 pM. In some embodiments, the affinity for a TfR ranges from about 50 pM to about 200 pM. For example, the affinity for a TfR may be about 25 pM, 50 pM, 100 pM, 150 pM or 200 pM. In some embodiments, the TfR affinity is for a human TfR (hTfR).

Methods for analyzing binding affinity, binding kinetics, and cross-reactivity are known in the art (see, e.g., the Examples). These methods include, but are not limited to, solid-phase binding assays (e.g., ELISA assay), immunoprecipitation, surface plasmon resonance (e.g., Biacore™ (GE Healthcare, Piscataway, NJ)), kinetic exclusion assays (e.g., KinExA®), flow cytometry, fluorescence-activated cell sorting (FACS), BioLayer interferometry (e.g., Octet™ (ForteBio, Inc., Menlo Park, CA)), and western blot analysis. In some embodiments, ELISA is used to determine binding affinity, binding kinetics, and/or cross-reactivity. Methods for performing ELISA assays are known in the art, and are also described in the Examples section below. In some embodiments, surface plasmon resonance (SPR) is used to determine binding affinity, binding kinetics, and/or cross-reactivity. In some embodiments, kinetic exclusion assays are used to determine binding affinity, binding kinetics, and/or cross-reactivity. In some embodiments, BioLayer interferometry assays are used to determine binding affinity, binding kinetics, and/or cross-reactivity. A non-limiting example of a method for determining binding affinity, as well as a non-limiting example of a method for determining the specific activity of an IgG:IDS fusion protein, are described in Example 2.

The concentration of fusion protein described herein in a peripheral organ (e.g., liver), the brain and/or plasma can be measured, for example, using a human transferrin receptor (hTfR) knock-in mouse model. Such a model can be used, for example, to measure and/or compare maximum brain concentration ($C_{max}$) and/or brain exposure, e.g., to determine whether $C_{max}$ is increased and/or brain exposure is prolonged. The creation of a human apical TfR ($TfR^{ms/hu}$) mouse knock-in model is described in U.S. Pat. No. 10,143,187. For evaluation of brain and/or plasma concentration or exposure of the fusion protein, the fusion protein can be administered to the mouse model (e.g., $TfR^{ms/hu}$). Plasma samples can be obtained from the mouse after a suitable period of time, followed by perfusion of the vascular system with a suitable solution. Following perfusion, peripheral organs or brains (or portions thereof) can be extracted and homogenized and lysed. Concentrations of the agent in the plasma and/or tissue (e.g., brain) lysate can then be determined using standard methods that will be known to one of ordinary skill in the art. As a non-limiting example, an ELISA-based assay, such as one described in Example 4, can be used to measure concentrations. By administering a range of doses to the knock-in mouse model, a standard curve can be generated.

A fusion protein described herein (e.g., IgG:IDS) may also be evaluated in various functional assays, in which the ability of the fusion protein to modulate a phenotype or behavior of a target cell is examined. A non-limiting example of an in vitro functional assay is described in Example 3, in which the cellular potency of an IgG:IDS fusion protein was evaluated in MPS II patient primary fibroblasts.

IDS activity may also be assessed by assaying a sample, such as a cell sample, tissue sample, or fluid sample (e.g., CSF or urine), for the amount of one or more glycosaminoglycans (GAGs) (e.g., heparan sulfate, dermatan sulfate, or total GAGs), which accumulate as a result of IDS deficiency. The amount of heparan and dermatan sulfate is determined by digesting GAGs present in a sample with heparinase and chondroitinase. The resulting disaccharides can then be assayed by mass spectrometry (e.g., LC-MS/MS). Samples with high levels of heparan and dermatan sulfate accumulation will have increased amounts of heparan and dermatan sulfate-derived disaccharides. Thus, the level of disaccharides is inversely proportional to IDS enzymatic activity. The mass spectrometry (e.g., LC-MS/MS) assay can be performed on any sample in which GAGs accumulate, including cell samples, tissue samples, and fluid samples. Such samples can be evaluated to monitor the activity of an IDS-containing protein described herein, e.g., that is administered to cells in vitro, or in some embodiments, administered to a subject in vivo. The subject may be an animal, such as a rodent, e.g., a mouse, or a non-human primate. In some embodiments, the subject is a human patient, such as a patient having Hunter syndrome that is undergoing treatment with an IDS therapy, wherein the assay is used to monitor IDS activity in the patient. In some embodiments, the human patient is undergoing treatment with a fusion protein described herein. An illustrative protocol for such an assay is described in Example 4.

Fusion Protein/Antibody Production

Methods of preparing a fusion protein, comprising an anti-TfR antibody linked to an IDS amino acid sequence, are known in the art and are also described in the Examples section below.

For example, the genes encoding the heavy and light chains of an antibody of interest can be cloned from a cell using recombinant methods and compositions, e.g., as described in U.S. Pat. No. 4,816,567. Thus, certain embodiments, provide a polynucleotide comprising a nucleotide sequence encoding an antibody or a fusion protein/fusion polypeptide, as described herein. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL (e.g., the light chain) of the antibody and an amino acid sequence comprising the heavy chain of the antibody linked to an IDS amino acid sequence via a peptide linker or peptide bond, or (2) a first vector comprising a nucleic acid that encodes an amino acid sequence comprising the VL (e.g., the light chain) of the antibody and a second vector comprising a nucleic acid that encodes an amino acid sequence comprising the heavy chain of the antibody linked to an IDS amino acid sequence via a peptide linker or peptide bond. In one embodiment, the host cell is eukaryotic, e.g. a Chinese Hamster Ovary (CHO) cell or lymphoid cell (e.g., Y0, NS0, Sp20 cell). Accordingly, certain embodiments provide a method for producing a fusion protein as described herein, comprising expressing one or more polynucleotides operable to express 1) a light chain as described herein; and 2) a heavy chain linked to an IDS amino acid sequence as described herein, in a host cell under conditions suitable for produce the fusion protein. Certain embodiments also provide a fusion protein produced by such a method.

For recombinant production of a fusion protein, a nucleic acid encoding a fusion protein/polypeptide, e.g., as described herein, is isolated and inserted into one or more vectors for further cloning and/or expression in a host cell. Such a nucleic acid may be readily isolated and sequenced using conventional procedures (e.g., by using oligonucleotide probes that are capable of binding specifically to genes encoding the heavy and light chains of the antibody/fusion protein).

Suitable host cells for cloning or expression of fusion protein-encoding vectors include prokaryotic or eukaryotic cells described herein. For example, fusion proteins may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, NJ, 2003), pp. 245-254, describing expression of antibody fragments in *E. coli*.) After expression, the fusion protein may be isolated from the bacterial cell paste in a soluble fraction and can be further purified. Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (HEK293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci.* USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

Compositions and Formulations

Guidance for preparing formulations for use in the present disclosure can be found in any number of handbooks for pharmaceutical preparation and formulation that are known to those of skill in the art.

In some embodiments, a pharmaceutical composition comprises a fusion protein as described herein and further comprises one or more pharmaceutically acceptable carriers and/or excipients. For example, in certain embodiments, the fusion protein is comprised within a pharmaceutical composition, which further comprises a pharmaceutically acceptable excipient. A pharmaceutically acceptable carrier includes any solvents, dispersion media, or coatings that are physiologically compatible and that do not interfere with or otherwise inhibit the activity of the active agent.

In some embodiments, the carrier is suitable for intravenous, intrathecal, intracerebroventricular, intramuscular, intraperitoneal, or subcutaneous administration. Pharmaceutically acceptable carriers can contain one or more physiologically acceptable compounds that act, for example, to stabilize the composition or to increase or decrease the absorption of the polypeptide. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are also available in the art.

The pharmaceutical compositions described herein can be manufactured, e.g., by means of conventional mixing, dissolving, granulating, dragee-making, emulsifying, encapsulating, entrapping, or lyophilizing processes. The following methods and excipients are exemplary.

As disclosed above, a fusion protein as described herein can be formulated for parenteral administration by injection, e.g., by bolus injection or continuous infusion. For injection, the fusion protein can be formulated into preparations by dissolving, suspending, or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers, and preservatives. In some embodiments, the fusion protein can be formulated in aqueous solutions, such as physiologically compatible buffers, non-limiting examples of which include Hanks's solution, Ringer's solution, and physiological saline buffer. Formulations for injection can be presented in unit dosage form, e.g., in ampules or in multi-dose containers, with an added preservative. The compositions can take such forms as suspensions, solutions, or emulsions in oily or aqueous vehicles, and can contain formulatory agents such as suspending, stabilizing, and/or dispersing agents. In some embodiments, the composition is a lyophilized composition. For example, a lyophilized composition (e.g., lyophilized powder or cake) may further comprise one or more excipients selected from the group consisting of a salt for adjusting osmolarity and/or pH (e.g., NaCl, $NaH_2PO_4$, $Na_2HPO_4$, NaOH, HCl), a cryo-lyoprotectant (e.g., trehalose, sucrose), a polymer (e.g., polyether polymer or block copolymer, such as polyethylene glycol, polypropylene glycol, polyethylene-polypropylene glycol), and a bulking agent (e.g., mannitol, glycine). A lyophilized composition may be reconstituted into an injectable liquid form prior to use (e.g., reconstituted via water, saline, or dextrose 5% water). In certain embodiments, the lyophilized composition may comprise excipients comprising $Na^+$, $Cl^-$, $PO_4^{3-}$, sucrose, and a block co-polymer polyethylene-polypropylene glycol.

Typically, a pharmaceutical composition for use in in vivo administration is sterile. Sterilization can be accomplished according to methods known in the art, e.g., heat sterilization, steam sterilization, sterile filtration, or irradiation.

Dosages and desired drug concentration of pharmaceutical compositions described herein may vary depending on the particular use envisioned. Certain suitable dosages are described herein.

Methods of Use

Insufficient or absent IDS enzyme activity leads to the accumulation of the glycosaminoglycans (GAGs) heparan sulfate (HS; e.g., D0A0 and D0S0) and dermatan sulfate (DS; e.g., D0a4) in the CNS and periphery, as well as lysosome dysfunction in multiple organs and tissues. Accordingly, certain embodiments provide a method of reducing levels of total GAGs or one or more GAG species in a subject in need thereof, comprising administering a fusion protein as described in herein (i.e., an IgG:IDS fusion protein described herein) or a pharmaceutical composition comprising such a fusion protein to the subject. In certain embodiments, a therapeutically effective amount of the fusion protein or a pharmaceutical composition comprising the fusion protein (e.g., about 1 mg/kg to about 10 mg/kg, such as about 1 mg/kg, 3 mg/kg or 10 mg/kg of protein) is administered to the subject.

The concentration of total GAGs or the concentration of one or more GAG species may also be evaluated in a subject having Hunter syndrome (e.g., in a physiological sample from the subject, e.g., a post-treatment sample from a subject administered a fusion protein described herein (e.g., IgG:IDS)). Such an evaluation may be used to assess disease activity or therapeutic response to a fusion protein described herein (e.g., IgG:IDS), including to identify and evaluate safe and therapeutically effective doses of the fusion protein (e.g., IgG:IDS). Quantification of GAG concentration levels may be performed using methods known in the art, for example, using a liquid chromatography mass spectrometry (LCMS) assay (see, e.g., Example 4).

In certain embodiments, the concentration of one or more GAG species may be evaluated and compared relative to a baseline level or control. The control or baseline level may vary; it is within the skill of the art to identify the appropriate control or baseline level depending on the parameter being evaluated. For example, in certain embodiments, the term "control" may refer to a healthy subject or a subject that does not have an IDS deficiency, or a sample therefrom. Alternatively, the term "control" may refer to a subject having an IDS deficiency (e.g., an IDS KO mouse or a Hunter syndrome patient) that was not administered the fusion protein. "Control" may also refer to a subject having an IDS deficiency prior to treatment (or a sample therefrom). Similarly, a "baseline level" may refer to a level or a range of levels that is measured in, e.g., a healthy subject or in a subject that does not have an IDS deficiency. In certain other embodiments described herein, a "baseline level" may also refer to a level or a range of levels in subject having an IDS deficiency that was not administered the fusion protein or in the subject prior to administration of the fusion protein. In certain embodiments, a control value or baseline level may be established using data from a population of control subjects. In some embodiments, the population of subjects is matched to a test subject according to one or more subject characteristics, such as age or sex. In some embodiments, the control value is established using the same type of sample from the population of subjects (e.g., a sample comprising blood or PBMCs) as is used for assessing the level of lipids/proteins in the test subject. In certain embodiments, a particular evaluation is performed, e.g., 7 days, 4 weeks, 12 weeks, 6 months, 12 months and/or 18 months after treatment initiation.

In certain embodiments, administration of a fusion protein described herein reduces levels of one or more GAG species in a sample from the subject as compared to a control. In certain embodiments, administration of a fusion protein described herein reduces levels of one or more GAG species in a sample from the subject by at least about 10%, 15%, 20%, 25%, 30%, 40%, 50%, 60%, 70%, 80%, 90%, 95% or more as compared to a control. In certain embodiments, the control is a subject having an IDS deficiency that was not administered the pharmaceutical composition. In certain embodiments, the control is the subject prior to treatment.

As used herein, the phrase "sample" or "physiological sample" is meant to refer to a biological sample obtained from a subject that contains an analyte of interest, such as a GAG species. Thus, the sample may be evaluated at, e.g., the molecular, lipid or protein level. In certain embodiments, the physiological sample comprises tissue, cerebrospinal fluid (CSF), urine, blood, serum, or plasma. In certain embodiments, the sample comprises tissue, such as brain, liver, kidney, lung or spleen. The sample may include a fluid. In certain embodiments, the sample comprises CSF. In certain embodiments, the sample comprises blood and/or plasma. In certain embodiments, the sample comprises serum. In certain embodiments, the sample comprises CNS tissue (e.g., brain tissue).

In certain embodiments, the administration of a fusion protein described herein reduces levels of one or more GAG species in an organ, tissue or fluid (e.g., blood, plasma, serum, CSF or urine) of the subject, as compared to a control. In certain embodiments, levels of one or more GAG species in an organ, tissue or fluid of the subject are reduced by at least about 10%, 15%, 20%, 25%, 30%, 40%, 50%, 60%, 70%, 80%, 90%, 95% or more, as compared to a control. In certain embodiments, the control is a subject having an IDS deficiency (e.g., Hunter syndrome) that was not administered the pharmaceutical composition. In certain embodiments, the control is the subject prior to treatment. For example, in certain embodiments, administration of a fusion protein described herein reduces levels of one or more GAG species in the CSF of the subject by at least about 10%, 15%, 20%, 25%, 30%, 40%, 50%, 60%, 70%, 80%, 90%, 95% or more (e.g., by at least about 30%, 40%, 50%, 60% or more), wherein the reduction is relative to the level of the corresponding one or more GAG species in the CSF of the subject prior to the administration. In certain embodiments, the administration reduces levels of one or more GAG species (e.g., HS, DS or total GAGs) in the CSF of the subject by at least about 10%, 15%, 20%, 25%, 30%, 40%, 50%, 60%, or 70%, wherein the reduction is relative to the level of the corresponding one or more GAG species (e.g., HS, DS or total GAGs) in the CSF of the subject prior to the administration.

In certain embodiments, the administration of a fusion protein described herein reduces levels of one or more GAG species in the CNS of the subject, as compared to a control. In certain embodiments, levels of one or more GAG species in the CNS of the subject is reduced by at least about 10%, 15%, 20%, 25%, 30%, 40%, 50%, 60%, 70%, 80%, 90%, 95% or more (e.g., by at least about 20%, 30%, 40%, or more), as compared to a control.

In certain embodiments, the administration of a fusion protein described herein reduces levels of one or more GAG species in the CSF of the subject, as compared to a control. In certain embodiments, levels of one or more GAG species in the CSF of the subject is reduced by at least about 10%, 15%, 20%, 25%, 30%, 40%, 50%, 60%, 70%, 80%, 90%, 95% or more (e.g., by at least about 30%, 40%, 50%, 60% or more), as compared to a control. In certain embodiments, the reduction of one or more GAG species in the CSF of the subject is relative to the CSF levels of the one or more GAG species in the subject prior to the administration.

In certain embodiments, the administration of a fusion protein described herein reduces levels of one or more GAG species in the serum of the subject, as compared to a control. In certain embodiments, levels of one or more GAG species in the serum of the subject are reduced by at least about 10%, 15%, 20%, 25%, 30%, 40%, 50%, 60%, 70%, 80%, 90%, 95% or more, as compared to a control. In certain embodiments, the reduction of one or more GAG species in the serum of the subject is relative to the serum levels of the one or more GAG species in the subject prior to the administration. In certain embodiments, the administration of a fusion protein described herein reduces levels of one or more GAG species in the serum of the subject to baseline levels (e.g. levels measured in a healthy subject or a subject that does not have an IDS deficiency (e.g., Hunter syndrome).

In certain embodiments, total GAG levels are reduced. In certain embodiments, heparan sulfate levels are reduced (e.g., D0A0 and/or D0S0 levels are reduced). In certain embodiments, dermatan sulfate levels are reduced (e.g., D0a4 levels are reduced).

Certain embodiments provide a fusion protein described herein or a pharmaceutical composition comprising such a fusion protein for use in a method of reducing one or more GAG species, the method comprising administering the fusion protein or pharmaceutical composition to a subject in need thereof. In certain embodiments, the method comprises administering a therapeutically effective amount of the fusion protein or a pharmaceutical composition comprising the fusion protein to the subject (e.g., a dose described herein, such as a dose of about 1 mg/kg, 3 mg/kg or 10 mg/kg of protein).

Certain embodiments provide the use of a fusion protein described herein in the preparation of a medicament for reducing one or more GAG species by administering the medicament to a subject in need thereof. In certain embodiments, the use is by administering a therapeutically effective amount of the medicament to a subject in need thereof (e.g., a dose described herein, such as a dose of about 1 mg/kg, 3 mg/kg or 10 mg/kg of protein).

Certain embodiments also provide a method of treating Hunter syndrome in a subject in need thereof, comprising administering a fusion protein as described herein or pharmaceutical composition comprising such a fusion protein to the subject.

Certain embodiments provide a fusion protein described herein or a pharmaceutical composition comprising such a fusion protein for use in medical therapy.

Certain embodiments provide a fusion protein described herein or a pharmaceutical composition comprising such a fusion protein for use in a method of treating Hunter syndrome, the method comprising administering the fusion protein or pharmaceutical composition to a subject in need thereof.

In certain embodiments, the method comprises administering a therapeutically effective amount of the fusion protein or a pharmaceutical composition comprising the fusion protein to the subject. For example, in certain embodiments, a dose as described herein, such as a dose of about 1 mg/kg, 3 mg/kg or 10 mg/kg of protein, is administered to the subject.

Certain embodiments also provide the use of a fusion protein described herein in the preparation of a medicament for treating Hunter syndrome by administering the medicament to a subject in need thereof. In certain embodiments, the use is by administering a therapeutically effective amount of the medicament to the subject (e.g., a dose described herein, such as a dose of about 1 mg/kg, 3 mg/kg or 10 mg/kg of protein).

Administration and Effective Doses

A fusion protein described herein or pharmaceutical composition comprising a fusion protein described herein may be administered to a subject, e.g., at an effective amount or dose, such as a therapeutically effect dose.

In some embodiments, the dose (e.g., effective dose or therapeutically effective dose) is from about 1 mg/kg to about 10 mg/kg of protein (e.g., about 1 mg/kg, about 2 mg/kg, about 3 mg/kg, 4 mg/kg, 5 mg/kg, 6 mg/kg, 7 mg/kg, 8 mg/kg, 9 mg/kg, or about 10 mg/kg). In some embodiments, the dose (e.g., effective dose or therapeutically effective dose) is from about 1 mg/kg to about 3 mg/kg of protein. In some embodiments, the dose (e.g., effective dose or therapeutically effective dose) is from about 3 mg/kg to about 10 mg/kg of protein. In certain embodiments, the dose (e.g., effective dose or therapeutically effective dose) is about 1 mg/kg of protein. In certain embodiments, the dose (e.g., effective dose or therapeutically effective dose) is about 3 mg/kg of protein. In certain embodiments, the dose (e.g., effective dose or therapeutically effective dose) is about 10 mg/kg of protein.

In certain embodiments, such a dose described herein is a therapeutically effective dose, such as a safe and therapeutically effective dose (e.g., a dose that results in the stabilization or decrease in urine total GAG concentration in the subject).

In certain embodiments, the pharmaceutical composition is administered weekly.

In some embodiments, a protein molecule described herein has an enzymatic activity of at least about 500 units (U)/mg, about 1,000 U/mg, or at least about 1,500, 2,000, 2,500, 3,000, 3,500, 4,000, 4,500, 5,000, 6,000, 7,000, 8,000, 9,000, or 10,000 U/mg. In some embodiments, the enzymatic activity is at least about 11,000 U/mg, or at least about 12,000, 13,000, 14,000, 15,000, 16,000, 17,000, 18,000, 19,000, 20,000, 25,000, 30,000, 35,000, 40,000, 45000, or 50,000 U/mg; or anywhere in a range of about 500 U/mg to about 50,000 U/mg.

Dosages may be varied according to several factors, including the chosen route of administration, the formulation of the composition, patient response, the severity of the condition, the subject's weight, the subject's age, the subject's head size and/or ratio of head size to height, and the judgment of the prescribing physician. The dosage can be increased or decreased over time, as required by an individual patient. In some embodiments, a patient initially is given a low dose, which is then increased to an efficacious dosage tolerable to the patient. Determination of an effective amount is well within the capability of those skilled in the art.

In various embodiments, a pharmaceutical composition described herein is administered parenterally. In some embodiments, the pharmaceutical composition is administered intravenously. Intravenous administration can be by infusion, e.g., over a period of from about 10 to about 30 minutes, or over a period of at least 1 hour, 2 hours, 3 hours, 4 hours, 6 hours, 8 hours, or 10 hours. In some embodiments, the pharmaceutical composition is administered intravenously over a period of from about 20 minutes to 6 hours, or from about 30 minutes to 4 hours. In some embodiments, the pharmaceutical composition is administered as an intravenous bolus. Combinations of infusion and bolus administration may also be used.

In certain embodiments the pharmacokinetics (PK) of the fusion protein (e.g., IgG:IDS) are evaluated. For example, PK parameters may include, but are not be limited to, the following: $C_{max}$; Trough concentration (Cmin); Tmax; Area under the concentration-time curve from time zero to the time of last quantifiable concentration ($_{Auc0-last}$); Area under the concentration-time curve over a dosing interval ($AUC_{0-\tau}$); Apparent terminal elimination rate constant ($\lambda z$); Apparent terminal elimination t1/2; and Accumulation ratio.

Articles of Manufacture

In another aspect, an article of manufacture comprising a fusion protein as described herein is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition and may have a sterile access port (for example the container may be an intravenous solution bag or a vial having a stopper pierceable by a hypodermic injection needle). At least one active agent in the composition is a fusion protein described herein. The label or package insert indicates that the composition is used for treating Hunter syndrome. Moreover, the article of manufacture may comprise (a) a first container with a composition contained therein, wherein the composition comprises fusion protein described herein; and (b) a second container with a composition contained therein, wherein the composition comprises a therapeutic agent. The article of manufacture in this embodiment may further comprise a package insert indicating that the compositions can be used to treat Hunter syndrome. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

Certain Definitions

Unless defined otherwise, technical and scientific terms used herein have the same meaning as commonly understood by one of ordinary skill in the art, and are consistent with: Singleton et al. (1994) Dictionary of Microbiology and Molecular Biology, 2nd Ed., J. Wiley & Sons, New York, NY; and Janeway, C., Travers, P., Walport, M., Shlomchik (2001) Immunobiology, 5th Ed., Garland Publishing, New York.

As used herein, the terms "about" and "approximately," when used to modify an amount specified in a numeric value or range indicate that the numeric value as well as reasonable deviations from the value known to the skilled person in the art, for example ±20%, ±10%, or ±5%, are within the intended meaning of the recited value.

The term "administer" refers to a method of delivering agents (e.g., such as an IgG:IDS fusion protein described herein), compounds, or compositions (e.g., pharmaceutical composition) to the desired site of biological action. These methods include, but are not limited to, oral, topical delivery, parenteral delivery, intravenous delivery, intradermal delivery, intramuscular delivery, intrathecal delivery, colonic delivery, rectal delivery, or intraperitoneal delivery. In one embodiment, the polypeptides described herein are administered intravenously.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (referred to as "Kd," "KD," or "$K_D$"). Affinity can be measured by common methods known in the art, including those described herein. Specific illustrative and exemplary embodiments for measuring binding affinity are described herein.

The term "amino acid" refers to naturally occurring and synthetic amino acids, as well as amino acid analogs and amino acid mimetics that function in a manner similar to the naturally occurring amino acids.

Naturally occurring amino acids are those encoded by the genetic code, as well as those amino acids that are later modified, e.g., hydroxyproline, γ-carboxyglutamate and O-phosphoserine.

Naturally occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids may be referred to herein by either their commonly known three letter symbols or by the one-letter symbols recommended by the IUPAC-IUB Biochemical Nomenclature Commission.

The term "antibody" refers to a protein with an immunoglobulin fold that specifically binds to an antigen via its variable regions. "Antibody" herein is used in the broadest sense and encompasses monoclonal antibodies, polyclonal antibodies, dimers, multimers, multispecific antibodies (e.g., bispecific antibodies), and antibody fragments, so long as they exhibit the desired biological activity (Miller et al. (2003) Jour. of Immunology 170:4854-4861). Antibodies may be murine, human, humanized, chimeric, or derived from other species. (Janeway, C., Travers, P., Walport, M., Shlomchik (2001) Immuno Biology, 5th Ed., Garland Publishing, New York). A target antigen generally has numerous binding sites, also called epitopes, recognized by CDRs (complementarity determining regions) on multiple antibodies. Each antibody that specifically binds to a different epitope has a different structure. Thus, one antigen may have more than one corresponding antibody. An antibody includes a full-length immunoglobulin molecule or a portion of a full-length immunoglobulin molecule that contains an antigen binding site that immunospecifically binds an antigen of a target of interest or part thereof (e.g., TfR). The immunoglobulin disclosed herein can be of any type (e.g., IgG, IgE, IgM, IgD, and IgA), class (e.g., $IgG_1$, $IgG_2$, $IgG_3$, $IgG_4$, $IgA_1$ and $IgA_2$) or subclass of immunoglobulin molecule. The immunoglobulins can be derived from any species. In one aspect, however, the immunoglobulin is of human, murine, or rabbit origin.

The terms "antibody that binds to TfR" and "anti-TfR antibody" refer to an antibody that is capable of binding TfR via its variable region with sufficient affinity such that the antibody is capable of binding TfR for transport across the blood-brain barrier. In one embodiment, the extent of binding of an anti-TfR antibody to an unrelated, non-TfR protein is less than about 10% of the binding of the antibody to TfR as measured, e.g., by a radioimmunoassay (RIA). In certain embodiments, an antibody that binds to TfR has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-TfR antibody binds to an epitope of TfR that is conserved among TfR from different species.

The terms "antigen-binding portion" and "antigen-binding fragment" are used interchangeably herein and refer to one or more fragments of an antibody that retains the ability to specifically bind to an antigen (e.g., TfR) via its variable region. Examples of antigen-binding fragments include, but are not limited to, a Fab fragment (a monovalent fragment consisting of the VL, VH, CL and CH1 domains), $F(ab')_2$ fragment (a bivalent fragment comprising two Fab fragments linked by a disulfide bridge at the hinge region), single chain Fv (scFv), disulfide-linked Fv (dsFv), complementarity determining regions (CDRs), a VL (light chain variable region), and a VH (heavy chain variable region).

The terms "CH3 domain" and "CH2 domain" as used herein refer to immunoglobulin constant region domain polypeptides. For purposes of this application, a CH3 domain polypeptide refers to the segment of amino acids from about position 341 to about position 447 as numbered according to EU, and a CH2 domain polypeptide refers to the segment of amino acids from about position 231 to about position 340 as numbered according to the EU numbering scheme and does not include hinge region sequences. CH2 and CH3 domain polypeptides may also be numbered by the IMGT (ImMunoGeneTics) numbering scheme in which the CH2 domain numbering is 1-110 and the CH3 domain numbering is 1-107, according to the IMGT Scientific chart numbering (IMGT website). CH2 and CH3 domains are part of the Fc region of an immunoglobulin. An Fc region refers to the segment of amino acids from about position 231 to about position 447 as numbered according to the EU numbering scheme, but as used herein, can include at least a part of a hinge region of an antibody. An illustrative hinge region sequence is the human IgG1 hinge sequence EPKSCDKTH-TCPPCP (SEQ ID NO:25).

The terms "control" or "control sample" refer to any sample appropriate to the detection technique employed. The control sample may contain the products of the detection technique employed or the material to be tested. Further, the controls may be positive or negative controls.

The term "chimeric" antibody refers to an antibody in which a portion of the heavy and/or light chain is derived from a particular source or species, while the remainder of the heavy and/or light chain is derived from a different source or species. In some embodiments, a chimeric antibody is a monoclonal antibody comprising a variable region from one source or species (e.g., mouse) and a constant region derived from a second source or species (e.g., human). Methods for producing chimeric antibodies are described in the art.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\gamma$, and $\mu$, respectively.

The term "complementarity determining region" or "CDR" refers to the three hypervariable regions in each chain that interrupt the four framework regions established by the light and heavy chain variable regions. The CDRs are primarily responsible for antibody binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 or CDR-H3 is located in the variable region of the heavy chain of the antibody in which it is found, whereas a VL CDR1 or CDR-L1 is the CDR1 from the variable region of the light chain of the antibody in which it is found.

The term "cross-reacts," as used herein, refers to the ability of an antibody to bind to an antigen other than the antigen against which the antibody was raised. In some embodiments, cross-reactivity refers to the ability of an antibody to bind to an antigen from a species different than the species of antigen against which the antibody was raised. As a non-limiting example, an anti-TfR antibody as described herein that is raised against a human TfR peptide can exhibit cross-reactivity with a TfR ortholog (e.g., monkey).

The phrase "effective amount" means an amount of a compound described herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "epitope" refers to the particular site on an antigen molecule to which an antibody binds. An epitope to which an antibody binds can be determined by epitope binning methods known in the art, such as, e.g. pair-wise combinatorial methods. In some embodiments, the particular site on an antigen molecule to which an antibody binds is determined by hydroxyl radical footprinting.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

A "Fab" fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of $F(ab')_2$. Other chemically crosslinked antibody fragments are also known to those skilled in the art. Pepsin digestion of an antibody yields two fragments; one is a $F(ab')_2$ fragment which comprises two antigen-binding domains and can cross-react with antigens, and the other is the remaining fragment (referred to as pFc'). Herein, an antibody fragment equivalent to that obtained by pepsin digestion is referred to as a "$F(ab')_2$-like antibody" when it comprises two antigen-binding domains and can cross-react with antigens. Such antibody fragments can also be produced, for example, by genetic engineering.

The term "Fc region" or "Fc polypeptide" herein is used to define a C-terminal region of an immunoglobulin heavy chain polypeptide that is characterized by an Ig fold as a structural domain. An Fc region contains a portion of the constant region, including at least the CH2 domain and/or the CH3 domain and may contain at least part of the hinge region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991. In general, an Fc region does not contain a variable region.

The term "FcRn" refers to the neonatal Fc receptor. Binding of Fc polypeptides to FcRn reduces clearance and increases serum half-life of the Fc polypeptide. The human FcRn protein is a heterodimer that is composed of a protein of about 50 kDa in size that is similar to a major histocompatibility (MHC) class I protein and a P2-microglobulin of about 15 kDa in size.

As used herein, an "FcRn binding site" refers to the region of an Fc polypeptide that binds to FcRn. In human IgG, the FcRn binding site, as numbered using the EU index, includes T250, L251, M252, 1253, S254, R255, T256, T307, E380, M428, H433, N434, H435, and Y436. These positions correspond to positions 20 to 26, 77, 150, 198, and 203 to 206 of SEQ ID NO:1.

As used herein, a "native FcRn binding site" refers to a region of an Fc polypeptide that binds to FcRn and that has the same amino acid sequence as the region of a naturally occurring Fc polypeptide that binds to FcRn.

"Framework" or "FR" refers to variable domain residues other than hypervariable region (HVR) residues that are relatively conserved within a species. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

A "fusion protein" or "antibody fusion protein" as used herein refers to an anti-TfR antibody (e.g., anti-human TfR antibody) that is linked or fused to an IDS enzyme, an IDS enzyme variant, or a catalytically active fragment thereof. As described herein, in certain embodiments, an IDS enzyme, an IDS enzyme variant, or a catalytically active fragment thereof (collectively referred to as "an IDS amino acid sequence") may be linked to the C-terminus of the heavy chain (i.e., heavy chain fusion polypeptide). One or both the heavy chains within the antibody may be linked to an IDS amino acid sequence. In certain embodiments, the fusion protein comprises an anti-TfR antibody comprising one heavy chain linked to an IDS amino acid sequence. In certain other embodiments, a fusion protein may comprise an anti-TfR antibody, wherein both heavy chains are each independently linked to an IDS amino acid sequence. The IDS enzyme, IDS enzyme variant, or catalytically active fragment thereof may be linked to the anti-TfR antibody by a peptide bond or by a polypeptide linker.

A "fusion polypeptide" or "heavy chain fusion polypeptide" as used herein refers to a heavy chain amino acid sequence that is linked (e.g., fused) to an IDS enzyme, an IDS enzyme variant, or a catalytically active fragment thereof. The heavy chain fusion polypeptide may be linked to the IDS enzyme, IDS enzyme variant, or catalytically active fragment thereof by a peptide bond or by a polypeptide linker.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" or a "fully human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., *supra*. In one embodiment, for the VH, the subgroup is subgroup III as in Kabat et al., *supra*.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, MD (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., *supra*.

The terms "identical" or percent "identity," in the context of two or more polypeptide sequences, refer to two or more sequences or subsequences that are the same or have a specified percentage of amino acid residues, e.g., at least 60% identity, at least 65%, at least 70%, at least 75%, at least 80%, at least 85%, at least 90%, at least 95%, at least 96%, at least 97%, at least 98%, or at least 99% or greater, that are identical over a specified region when compared and aligned for maximum correspondence over a comparison window, or designated region, as measured using a sequence comparison algorithm or by manual alignment and visual inspection.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

The terms "corresponding to," "determined with reference to," or "numbered with reference to" when used in the context of the identification of a given amino acid residue in a polypeptide sequence, refers to the position of the residue of a specified reference sequence when the given amino acid sequence is maximally aligned and compared to the reference sequence. The polypeptide that is aligned to the reference sequence need not be the same length as the reference sequence.

An "iduronate sulfatase," "iduronate-2-sulfatase," or "IDS" as used herein refers to iduronate 2-sulfatase (EC 3.1.6.13), which is an enzyme involved in the lysosomal degradation of the glycosaminoglycans heparan sulfate and dermatan sulfate. Deficiency of IDS is associated with Mucopolysaccharidosis II, also known as Hunter syndrome. The term "IDS" or "IDS enzyme" as used herein, optionally as a component of a fusion protein that comprises an anti-TfR antibody, is catalytically active and encompasses wild-type IDS and functional variants, including allelic and splice variants, and catalytically active fragments thereof. The sequence of human IDS isoform I, which is the human sequence designated as the canonical sequence, is available under UniProt entry P22304 and is encoded by the human IDS gene at Xq28. The full-length sequence is provided as SEQ ID NO:1. A "mature" IDS sequence as used herein refers to a form of a polypeptide chain that lacks the signal and propeptide sequences of the naturally occurring full-length polypeptide chain. The amino acid sequence of a mature human IDS polypeptide is provided as SEQ ID NO:2, which corresponds to amino acids 34-550 of the full-length human sequence. A "truncated" IDS sequence as used herein refers to a catalytically active fragment of the naturally occurring full-length polypeptide chain. The amino acid sequence of an exemplary truncated human IDS polypeptide is provided as SEQ ID NO:3, which corresponds to amino acids 26-550 of the full-length human sequence. The structure of human IDS has been well-characterized. An illustrative structure is available under PDB accession code 5FQL. The structure is also described in Nat. Comm. 8:15786 doi: 10.1038/ncomms15786, 2017. Non-human primate IDS sequences have also been described, including chimpanzee (UniProt entry K7BKV4) and rhesus macaque (UniProt entry H9FTX2). A mouse IDS sequence is available under Uniprot entry Q08890. An IDS variant has at least 50%, at least 55%, at least 60%, at least 65%, at least 70%, at least 75%, at least 80%, at least 85%, at least 90%, or at least 95% of the activity of the corresponding wild-type IDS or fragment thereof, e.g., when assayed under identical conditions. A catalytically active IDS fragment has at least 50%, at least 55%, at least 60%, at least 65%, at least 70%, at least 75%, at least 80%, at least 85%, at least 90%, or at least 95% of the activity of the corresponding full-length IDS or variant thereof, e.g., when assayed under identical conditions.

An "IDS enzyme variant" refers to a functional variant, including allelic and splice variants, of a wild-type IDS enzyme or a fragment thereof, where the IDS enzyme variant has at least 50%, at least 55%, at least 60%, at least 65%, at least 70%, at least 75%, at least 80%, at least 85%, at least 90%, or at least 95% of the activity of the corresponding wild-type IDS enzyme or fragment thereof, e.g., when assayed under identical conditions.

An "immunoconjugate" is an antibody conjugated to one or more heterologous molecule(s).

The term "individual," "subject," and "patient," as used interchangeably herein, refers to a mammal, including but not limited to humans, non-human primates, rodents (e.g., rats, mice, and guinea pigs), rabbits, cows, pigs, horses, and other mammalian species. In certain embodiments described herein, the subject is a human subject. In certain embodiments, the subject is a male subject.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., $IgG_1$, $IgG_2$, $IgG_3$, $IgG_4$, IgA, and $IgA_2$. The heavy-chain constant domains that correspond to the different classes of antibodies are called α, δ, ε, γ, and μ, respectively. The subunit structures and three-dimensional configurations of different classes of immunoglobulins are well known. Ig forms include hinge-modifications or hingeless forms (Roux et al. (1998) J. Immunol. 161:4083-4090; Lund et al. (2000) Eur. J. Biochem. 267: 7246-7256; US 2005/0048572; US 2004/0229310).

An "isolated" antibody is one which has been separated from a component of its natural environment. In some embodiments, an antibody is purified to greater than 90%, 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-TfR antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies described herein may be made by the hybridoma method first described by Kohler et al. (1975) Nature 256:495, or may be made by recombinant DNA methods (see for example: U.S. Pat. Nos. 4,816,567; 5,807,715). The monoclonal antibodies may also be isolated from phage antibody libraries using the techniques described in Clackson et al. (1991) Nature, 352:624-628; Marks et al. (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

As used herein, the term "mutant" with respect to a mutant polypeptide or mutant polynucleotide is used interchangeably with "variant." Mutations may include substitutions, insertions, and deletions.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (x) and lambda (k), based on the amino acid sequence of its constant domain.

The terms "obtaining a sample from a patient", "obtained from a patient" and similar phrasing, is used to refer to obtaining the sample directly from the patient, as well as obtaining the sample indirectly from the patient through an intermediary individual (e.g., obtaining the sample from a courier who obtained the sample from a nurse who obtained the sample from the patient).

The term "package insert" is used to refer to instructions customarily included in commercial packages of research tools or therapeutic products, that contain information about the conditions for use, indications, usage, dosage, administration, combination therapy, contraindications and/or warnings concerning the use of such products.

The term "pharmaceutical formulation" refers to a preparation which is in such form as to permit the biological activity of an active ingredient contained therein to be effective, and which contains no additional components which are unacceptably toxic to a subject to which the formulation would be administered.

The term "pharmaceutically acceptable excipient" refers to a non-active pharmaceutical ingredient that is biologically or pharmacologically compatible for use in humans or animals, such as but not limited to a buffer, carrier, or preservative.

The terms "polypeptide" and "peptide" are used interchangeably herein to refer to a polymer of amino acid residues in a single chain. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

The term "protein" as used herein refers to either a polypeptide or a dimer (i.e, two) or multimer (i.e., three or more) of single chain polypeptides. The single chain polypeptides of a protein may be joined by a covalent bond, e.g., a disulfide bond, or non-covalent interactions.

The term "polynucleotide" and "nucleic acid" interchangeably refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. Examples of polynucleotides contemplated herein include single- and double-stranded DNA, single- and double-stranded RNA, and hybrid molecules having mixtures of single- and double-stranded DNA and RNA.

A "binding affinity" as used herein refers to the strength of the non-covalent interaction between two molecules, e.g., a single binding site on a polypeptide and a target, e.g., transferrin receptor, to which it binds. Thus, for example, the term may refer to 1:1 interactions between a polypeptide and its target, unless otherwise indicated or clear from context. Binding affinity may be quantified by measuring an equilibrium dissociation constant ($K_D$), which refers to the dissociation rate constant ($k_d$, time$^{-1}$) divided by the association rate constant ($k_a$, time$^{-1}$ M$^{-1}$). $K_D$ can be determined by measurement of the kinetics of complex formation and dissociation, e.g., using Surface Plasmon Resonance (SPR) methods, e.g., a Biacore™ system; kinetic exclusion assays such as KinExA®; and BioLayer interferometry (e.g., using the ForteBio® Octet® platform). As used herein, "binding affinity" includes not only formal binding affinities, such as those reflecting 1:1 interactions between a polypeptide and its target, but also apparent affinities for which $K_D$'s are calculated that may reflect avid binding.

As used herein, the term "specifically binds" or "selectively binds" to a target, e.g., TfR, when referring to a TfR-binding antibody as described herein or a fusion protein comprising such an antibody, refers to a binding reaction whereby the TfR-binding antibody or fusion protein binds to the target with greater affinity, greater avidity, and/or greater duration than it binds to a structurally different target. In typical embodiments, the TfR-binding antibody or fusion protein has at least 5-fold, 10-fold, 50-fold, 100-fold, 1,000-fold, 10,000-fold, or greater affinity for a specific target, e.g., TfR, compared to an unrelated target when assayed under the same affinity assay conditions. The term "specific binding," "specifically binds to," or "is specific for" a particular target (e.g., TfR), as used herein, can be exhibited, for example, by a molecule having an equilibrium dissociation constant $K_D$ for the target to which it binds of, e.g., $10^{-4}$ M or smaller, e.g., $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In some embodiments, a TfR-binding antibody or fusion protein specifically binds to an epitope on TfR that is conserved among species, (e.g., structurally conserved among species), e.g., conserved between non-human primate and human species (e.g., structurally conserved between non-human primate and human species). In some embodiments, a TfR-binding antibody or fusion protein may bind exclusively to a human TfR.

A "transferrin receptor" or "TfR" as used herein refers to transferrin receptor protein 1. The human transferrin receptor 1 polypeptide sequence is set forth in SEQ ID NO:26. Transferrin receptor protein 1 sequences from other species are also known (e.g., chimpanzee, accession number XP_003310238.1; rhesus monkey, NP_001244232.1; dog, NP_001003111.1; cattle, NP_001193506.1; mouse, NP_035768.1; rat, NP_073203.1; and chicken, NP_990587.1). The term "transferrin receptor" also encompasses allelic variants of exemplary reference sequences, e.g., human sequences, that are encoded by a gene at a transferrin receptor protein 1 chromosomal locus. Full-length transferrin receptor protein includes a short N-terminal intracellular region, a transmembrane region, and a large extracellular domain. The extracellular domain is characterized by three domains: a protease-like domain, a helical domain, and an apical domain. The apical domain sequence of human transferrin receptor 1 is set forth in SEQ ID NO:27.

As used herein, "treatment" (and grammatical variations thereof such as "treat" or "treating") refers to clinical intervention to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis.

A "therapeutically effective amount" of a substance/molecule disclosed herein may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome using methods generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and which may contain a foreign gene integrated into their chromosome. The term "untransformed" refers to normal cells that have not been through the transformation process.

A "transgenic" organism is an organism having one or more cells that contain an expression vector.

The term "variable region," "variable domain," "V region," or "V domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides described herein may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art.

The term "conservative substitution," "conservative mutation," or "conservatively modified variant" refers to an alteration that results in the substitution of an amino acid with another amino acid that can be categorized as having a similar feature. Examples of categories of conservative amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R), and His (Histidine or H); an "aromatic group" including Phe (Phenylalanine or F), Tyr (Tyrosine or Y), Trp (Tryptophan or W), and (Histidine or H); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T), and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr, and Cys.

Examples of categories of conservative mutations include amino acid substitutions of amino acids within the subgroups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH₂ can be maintained. In some embodiments, hydrophobic amino acids are substituted for naturally occurring hydrophobic amino acid, e.g., in the active site, to preserve hydrophobicity.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Wild-type" refers to the normal gene, or organism found in nature without any known mutation.

The following Examples are intended to be non-limiting.

Example 1: Construction of IgG:IDS

Cloning and Architecture

The IgG:IDS molecule contains a TfR antibody that is linked to two IDS enzymes. One IDS enzyme is linked to the C-terminus of each Fc portion of the TfR antibody heavy chain by a peptide linker (FIG. 1). The antibody constant regions in IgG:IDS were human IgG₁. The heavy chain-IDS sequence is represented by SEQ ID NO:17 or SEQ ID NO:18, and the light chain sequence is represented by SEQ ID NO:5.

Protein Expression

The IgG:IDS construct was expressed via transient transfection of ExpiCHO cells (Thermo Fisher Scientific) according to manufacturer's instructions. Cultures were co-transfected with plasmids encoding IgG:IDS (heavy chain and light chains) and SUMF1 cDNAs at a ratio of 2:2:1.

Protein Purification

IgG:IDS was purified to homogeneity from serum-free CHO cultures by a series of chromatographic steps. IgG:IDS was affinity purified using Protein A followed by anion-exchange chromatography. Final fractions with both a high degree of purity and relatively enriched for negatively charged post-translational modifications (PTMs) (e.g., about 12-19 mol/mol sialic acid:fusion protein), as assessed by analytical size-exclusion chromatography (SEC) and/or microcapillary electrophoresis and LCMS), were pooled, concentrated and dialyzed into 20 mM sodium phosphate, pH 6.5 and 130 mM NaCl. Preparations were stored at 4° C. or −80° C. prior to use and routinely analyzed by SEC, specific activity and for endotoxin content.

Example 2: Characterization of IgG:IDS $K_D$ Determination Using Surface Plasmon Resonance (SPR)

The affinity of IgG:IDS for human transferrin receptor (hTfR) was determined by surface plasmon resonance on a Biacore™ T200 instrument using two methods, similar to previously described (Kariolis et al. 2020. *Sci Transl Med* 12(545):eaay1359). In Method 1, to evaluate monovalent TfR binding affinity, IgG:IDS was captured on a Protein A-coated Biacore™ Series S CM5 sensor chip and serial dilutions of the apical domain of hTfR (hTfR$^{apical}$) were injected over the captured sample. In Method 2, for evaluation of apparent hTfR binding affinity of IgG:IDS, biotinylated full-length hTfR was immobilized on a streptavidin-coated CM5 sensor chip, followed by injection of serial dilutions of IgG:IDS. For both methods, the single-cycle kinetics mode was used for sample injection (association time, 90 s; dissociation time, 600 s), and binding affinities were calculated using Biacore™ T200 Evaluation Software v3.0.

Using SPR, it was observed that IgG:IDS can bind TfR bivalently and was strongly influenced by receptor density. IgG:IDS was measured as having a monovalent affinity of 2.6 nM to hTfR$^{apical}$ and an apparent affinity of ~100 pM to the full-length receptor.

In Vitro IDS Activity

The specific activity of IgG:IDS was measured with a two-step fluorometric enzymatic assay using an artificial substrate as previously described (Ullman et al. 2020. *Sci Transl Med* 12(545):eaay1163). In brief, a 4-Methylumbelliferone (leaving group) standard curve was fit by linear regression to calculate the amount of product and verified as less than 10% of total substrate cleavage. Specific activity pmol product/minute/mg of protein was calculated.

Based on the in vitro activity assay, the specific activity of IgG:IDS was highly active and measured at about 4400 pmol product/minute/mg of protein (averaged over n=5 measurements).

Mannose-6-Phosphate Binding

ELISA plates were coated with an Fc fusion of the 9$^{th}$ domain of human cation independent mannose-6-phosphate receptor (ciM6PR; Uniprot P11717) at 1 g/mL in PBS overnight at 4° C. The following day, the plate was washed three times with wash buffer (PBS with 0.02% Tween-20) and blocking buffer (PBS with 0.02% Tween-20 and 5% BSA) was added to each well. Blocking was carried out for 1 hour at room temperature after which the plate was washed three times, and IgG:IDS was added to the first column of the plate at a concentration of 25 nM. A 3-fold serial dilution was performed across the plate. Primary incubation of the binding reactions was carried out for one hour at room temperature. After binding, the plate was washed three times, and binding was detected using biotinylated anti-IDS antibody diluted to 0.0625 g/mL in sample buffer. The plate was incubated with a detection antibody for one hour at room temperature and then washed three times. Streptavidin-HRP, diluted 1:50,000 in sample buffer, was then added to each well. The plate was incubated for 30 minutes at room temperature and then washed three times. The ELISA was developed using TMB reagent. The ELISA plate was read on a HighRes BioTek Synergy plate reader, where the absorbance at 450 nm was recorded.

Figure 2:
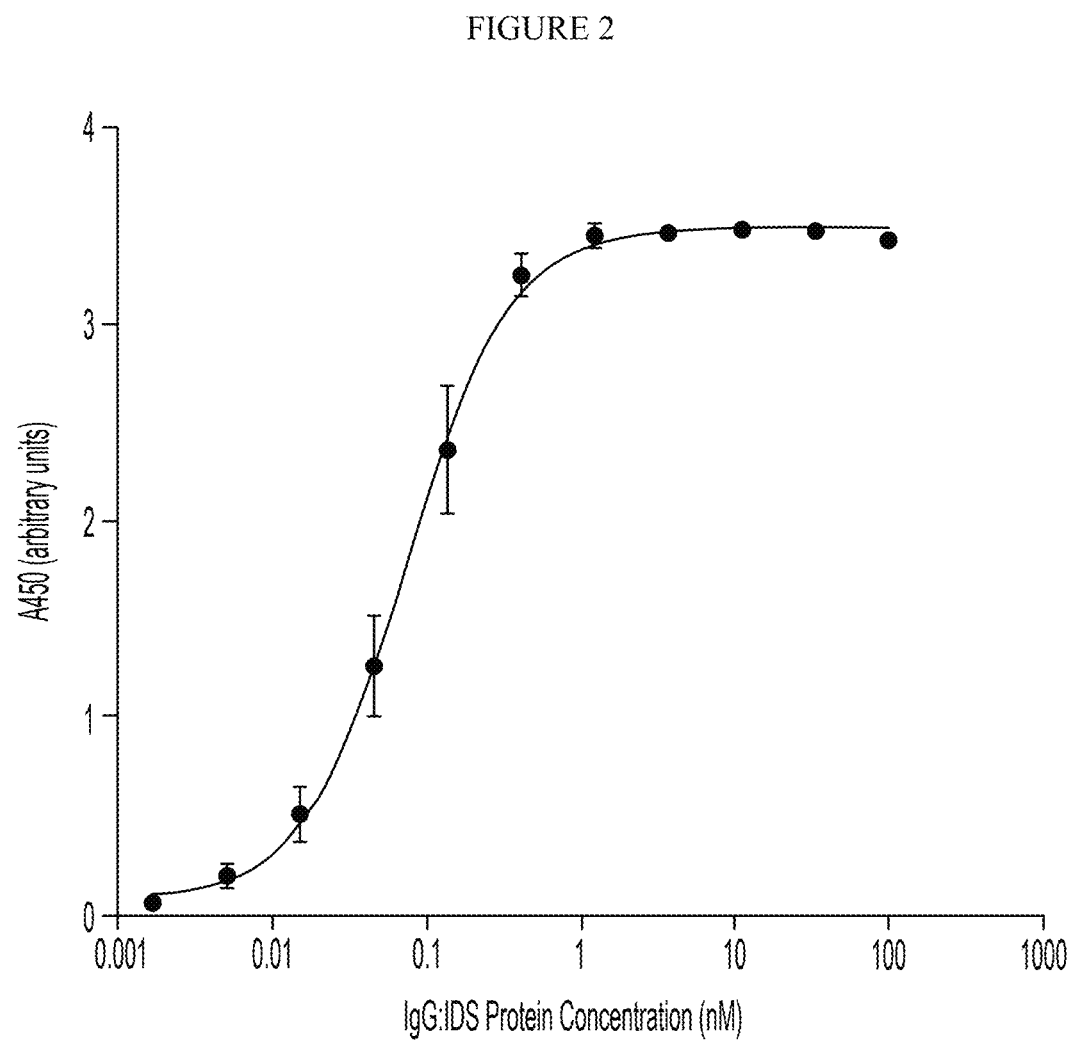

Based on the ELISA binding assay, binding of IgG:IDS to mannose-6-phosphate receptor was measured with EC50 of about from about 55 to 76 pM. A representative binding curve for IgG:IDS is illustrated in FIG. 2.

Example 3: Pharmacokinetic Characterization of IgG:IDS

S$^{35}$-Sulfate Accumulation Assay to Assess Cellular Potency

The cellular activity of IgG:IDS was assessed in MPS II patient-derived fibroblasts using a an $^{35}$S pulse-chase assay, in which $^{35}$S is integrated into newly-synthesized GAGs (Ullman et al. 2020. *Sci Transl Med* 12(545):eaay1163). MPS II patient (GM01928, GM12366, GM01583) primary fibroblasts, were obtained from Coriell. The cellular S$^{35}$-accumulation assay was performed using a method modified from Lu and co-workers (Lu et al. 2010. *Bioconjug Chem* 21:151-156). Briefly, fibroblasts were plated at 25,000 cells/well in 96-well plates and grown in DMEM high glucose (Gibco) with 10% FBS (Sigma). After 3 days of culture, media was replaced with low-sulfate F12 medium (Gibco) supplemented with 10% dialyzed fetal bovine serum and 40 mCi/mL [S35] sodium sulfate (PerkinElmer) for 96 hours. Following [S35] sodium sulfate incubation, cells were treated with IgG:IDS. After 24 hours of incubation, media was aspirated, cells were washed with cold PBS, and lysed with 0.01 N NaOH. Incorporated S35 was measured by scintillation counting (Microbeta Trilux). EC50 curves were generated using Prism software using a log(agonist) vs. response, variable slope (four parameter) fit.

Figure 3:
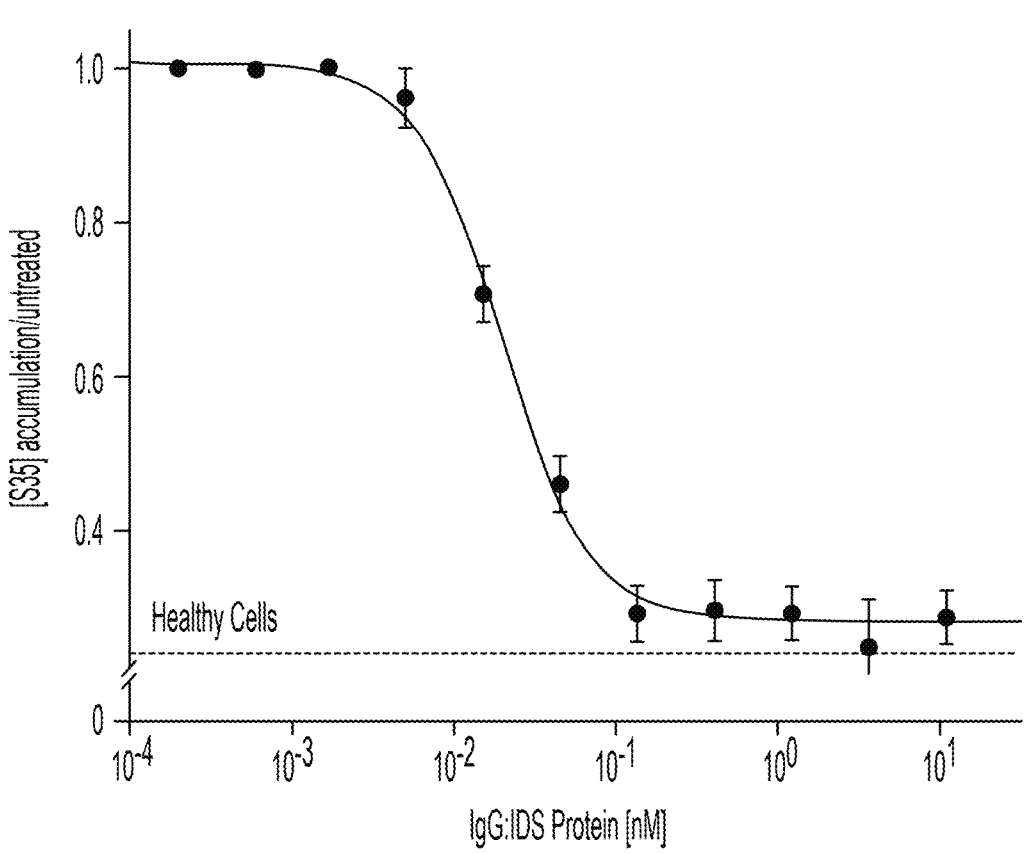
FIG. 3 illustrates the cellular potency of IgG:IDS in MPSII fibroblasts. A $S^{35}$-sulfate accumulation assay was used to generate the representative cellular potency curve for IgG:IDS (averaged across the cell lines).

IgG:IDS was found to be highly active in this assay, reducing accumulation of $^{35}$S-labelled substrates with cellular EC50 values ranging from about 16 pM to 23 pM (see, Table 1). The data illustrate that IgG:IDS was effectively internalized and reduced substrate accumulation in MPS II patient-derived cells in the low pM range. A representative cellular potency curve for IgG:IDS (averaged across the cell lines) is illustrated in FIG. 3.

TABLE 1

| IgG:IDS Cellular Potency | |
| --- | --- |
| | EC$_{50}$ (pM) |
| MPSII Patient-Derived Cell Line GM01583 | 16 |
| MPSII Patient-Derived Cell Line GM01928 | 21.2 |
| MPS II Patient-Derived Cell Line GM12366 | 23.1 |

Liquid Chromatography-Mass Spectrometry Analysis of Mannose-6-Phosphate (M6P) and Sialic Acid (SA)

Recombinant purified IgG:IDS protein (5 pg) was buffer exchanged into 50 mM ammonium acetate, pH 7.2. Normalized amount of protein was spiked with stable isotope labeled (SIL)$^{13}$C6 mannose-6-phosphate (SIL-M6P, Omicronbio Inc, Cat #, MAN-05, 62.5 ng per sample) and $^{13}$C3-sialic acid (SIL-SA, Omicronbio Inc, Catalog #NEU-004, 200 ng per sample) as an internal standard then hydrolyzed or digested for analysis. M6P was hydrolyzed from proteins using 150 µL of a 6.6M trifluoroacetic acid solution at 90° C. heater block for 90 minutes while shaking. Speed vacuumed samples were then washed with acetonitrile (ACN) once and dried down. Final pellets resuspended in 50 µL ACN:water (20:80, v:v) were analyzed by LC-MS/MS. SA was digested from the protein by SialEXO Enzyme (Genovis). Briefly, 5 µg of protein were mixed with 10 µL of SIL-SA at 20 ng/µL, add 3 µL of 1 M Tris buffer at pH 7.5, make up to 60 µL by MiliQ water, then add 1 µL of SialEXO (10 unit/µL), incubate at 37 C for 2 hours. SA samples were injected without further process.

M6P and SA analyses were performed by liquid chromatography on UHPLC Vanquish (Thermo Scientific, CA, USA) coupled to UV/Vis and Q Exactive Orbitrap electrospray ionization mass spectrometer (Thermo Scientific, CA, USA). Samples were injected on a ACQUITY UPLC BEH Amide 1.7 mm, 2.1×150 mm column (Waters Corporation) and analyzed by negative ionization mode mass spectrometry with a mobile phase of (A) water with 0.1% Formic Acid and (B) Acetonitrile with 0.1% formic acid using a 4.5-min gradient, starting with 60% B, then 42% B at 1.8 min, drop to 10% B at 2.2 min and hold to 3 min, then ramp up to 60% B and hold to 4.5 min. The flow rate is 0.45 mL/min and column temperature 60 C.

Data was collected using parallel reaction monitoring (PRM) acquisition under negative mode including M6P and SIL-M6P internal standards. The inclusion list is: 259.0224 and 265.0426 (negative ions) from 1.6 to 2.2 min for M6P and SIL-M6P, respectively; 308.0992 and 311.175 (negative ions) from 1.0 to 1.6 min for SA and SIL-SA, respectively. AUC ratios of M6P/SIL-M6P and SA/SIL-SA were used to calculate the molecular amount of M6P and SA, and the mol/mol of M6P:protein and mol/mol of SA:protein were obtained.

The measured M6P content of IgG:IDS ranged from about 1.5 mol/mol to 2.3 mol/mol of M6P:protein. The measured sialic acid content of IgG:IDS was about 15-16 mol/mol of SA:protein.

Example 4: Administration of IgG:IDS Reduces Brain and CSF GAGs in IDS KO; TfR$^{mu/Hu}$ Mice Materials and Methods Animal Care Mice were housed under a 12-hour light/dark cycle and had access to water and standard rodent diet (LabDiet® #25502, Irradiated) ad libitum.

Mouse Strains

A previously described, Ids KO mice on a B6N background were obtained from The Jackson Laboratories (JAX strain 024744). Development and characterization of the TfR$^{mu/hu}$ KI mouse line harboring the human TfR apical domain knocked into the mouse receptor was previously described (U.S. Pat. No. 10,143,187). TfR$^{mu/hu}$ male mice were bred to female Ids heterozygous mice to generate Ids KO; TfR$^{mu/hu}$ KI mice. All mice used in this study were males.

Pharmacokinetics (PK) of IgG:IDS 2-3 month old TfR$^{mu/hu}$ KI mice (n=3 per group) were injected with 1 mg/kg, 3 mg/kg, or 10 mg/kg body weight of IgG:IDS via the tail vein and sacrificed at 0.5, 4, 8, and 24 hours post dose. For terminal sample collection, animals were deeply anesthetized via intraperitoneal (i.p.) injection of 2.5% Avertin. Blood was collected via cardiac puncture for serum collection and allowed to clot at room temperature for at least 30 minutes. Tubes were then centrifuged at 12,700 rpm for 7 minutes at 4° C. Serum was transferred to a fresh tube and flash-frozen on dry ice. Animals were transcardially perfused with ice-cold PBS using a peristaltic pump (Gilson Inc. Minipuls Evolution), and the brain and liver were dissected. Liver and brain tissue (50 mg) were flash-frozen on dry ice and prepared for an IDS/IDS ELISA as described below.

Tissue Preparation for PK Analysis

Tissue (50 mg) was homogenized in 10× volume by tissue weight cold 1% NP40 lysis buffer (1 mL 10% NP-40 Surfact-Amps detergent solution, 9 mL 1×PBS, 1 tablet cOmplete protease inhibitor, 1 tablet PhosSTOP protease inhibitor) with a 3 mm stainless steel bead using the Qiagen TissueLyzer II for two rounds of 3 minutes at 27 Hz. Homogenates were then incubated on ice for 20 minutes and spun at 14,000 rpm for 20 minutes at 4° C. The resulting lysate was transferred to a single use aliquot and stored at −80° C.

IDS:IDS ELISA and PK Analysis

IgG:IDS was measured in serum, liver lysates, and brain lysates using an Iduronate-2-Sulfatase sandwich ELISA. A 384-well maxisorp plate (Thermo, Cat #464718) was coated overnight with an anti-ID S antibody (R&D Systems, Cat #AF2449) and blocked with Casein-PBS Buffer (Thermo, Cat #37528) the following day. Samples containing IgG:IDS were added to the plate and incubated for one hour at room temperature. After a subsequent wash, a biotinylated anti-IDS antibody (R&D Systems, Cat #BAF2449) was added to capture the immobilized IgG:IDS and IgG:IDS. The IDS sandwich was then detected with a streptavidin-horseradish peroxidase conjugate (Jackson Immuno Research, Cat #016-030-084) followed by incubation with a 3,3',5,5'tetramethyl-benzidine (TMB) substrate (Thermo, Cat #34028). The reaction was quenched with 4N hydrosulfuric acid (Life Technologies, Cat #SS04) and the plate was read at 450 nm absorbance wavelength on a plate spectrophotometer. The TMB color development is directly proportional to the concentration of IgG:IDS in the samples. A calibration curve was generated using a 5-Parameter Logistic Fit with an assay range of 0.00137 nM-1 nM. Serum, liver, and brain exposures for IgG:IDS were calculated using NCA from the Vortex module from Dotmatics version 4.8 (Bishop's Stortford, UK). Semi-log linear graphs and tabular results with standard deviation was curated with Prism 8 (GraphPad, San Diego, CA).

Pharmacodynamics of IgG:IDS 2-3 month old TfR$^{mu/hu}$ KI (n=5 per group) and Ids KO; TfR$^{mu/hu}$ mice (n=5 per group) were administered a single dose of 0, 1 mg/kg, 3 mg/kg, or 10 mg/kg body weight of IgG:IDS via the tail vein and sacrificed 7 days post dose. For terminal sample collection, animals were deeply anesthetized via intraperitoneal injection of 2.5% Avertin. For CSF collection, a sagittal incision was made at the back of the animal's skull, subcutaneous tissue and muscle was separated to expose the cisterna *magna* and a pre-pulled glass capillary tube was used to puncture the cisterna *magna* to collect CSF. CSF was transferred to a Low Protein LoBind Eppendorf tube and centrifuged for 10 minutes at 4° C. CSF was transferred to a fresh tube and snap frozen on dry ice. Lack of blood contamination in mouse CSF was confirmed by measuring the absorbance of the samples at 420 nm. Blood, serum and tissues were obtained as described above and flash frozen on dry ice.

Tissue and Fluid Preparation for Pharmacodynamic GAG Analysis 50 mg tissue was homogenized in 750 μL water using the Qiagen TissueLyzer II for three minutes at 30 Hz. Homogenate was transferred to a 96-well deep plate and sonicated using a 96-tip sonicator (Q Sonica) for 10×1 second pulses. Sonicated homogenates were spun at 2,500×g for 30 minutes at 4° C. The resulting lysate was transferred to a clean 96-well deep plate, and a BCA was performed to quantify total protein. 10 pg total protein lysate or 3 μL of CSF was used for subsequent HS/DS digestion. Digestion was carried out in a PCR plate as follows: Internal standard mix of HS and DS (20 ng total) were added to each sample and mixed with Heparinases I, II, III and Chondriotinase B in digestion buffer for 3 hours with shaking at 30° C. After digestion, EDTA was added to each sample and the mixture was boiled at 95° C. for 10 minutes. The digested samples were spun for 5 minutes, and samples were transferred to a cellulose acetate filter plate (Millipore, MSUN03010) and spun for 5 minutes. The resulting flow through was mixed with equal parts of acetonitrile in glass vials and analyzed by mass spectrometry as described below.

Mass Spectrometry Analysis of GAGs

Quantification of GAG was performed by liquid chromatography (Shimadzu Nexera X2 system, Shimadzu Scientific Instrument, Columbia, MD, USA) coupled to electrospray mass spectrometry (Sciex QTRAP 6500+, Sciex, Framingham, MA, USA). For each analysis, sample was injected on a ACQUITY UPLC BEH Amide 1.7 mm, 2.1×150 mm column (Waters Corporation) using a flow rate of 0.55 mL/minute with a column temperature of 55° C. Mobile phases A and B consisted of water with 10 mM ammonium formate and 0.1% formic acid, and acetonitrile with 0.1% formic acid, respectively. A gradient was programmed as follows: 0.0-0.5 minutes at 80% B, 0.5-3.5 minutes from 80% B to 50% B, 3.5-4.0 minutes 50% B to 80% B, 4.0-4.5 minutes hold at 80% B. Electrospray ionization was performed in the negative-ion mode applying the following settings: curtain gas at 25; collision gas was set at medium; ion spray voltage at −4500; temperature at 600° C.; ion source Gas 1 at 50; ion source Gas 2 at 60. Data acquisition was performed using Analyst 1.6.3 (Sciex) in multiple reaction monitoring mode (MRM), with dwell time 50 (msec) for each species. collision energy (CE) was set at −30; declustering potential (DP) at −80; entrance potential (EP) at −10; collision cell exit potential (CXP) at −10. GAGs were detected as [M-H]-using the following MRM transitions: D0A0 at m/z 378.1>87.0; D0S0 at m/z 416.1>138.0; D0a4 at m/z 458.1>300.0; D4UA-2S-GlcNCOEt-6S (Iduron Ltd, Manchester, UK) at m/z 472.0 (in source fragment ion) >97.0 was used as internal standard. Individual disaccharide species were identified based on their retention times and MRM transitions using commercially available reference standards (Iduron Ltd). GAGs were quantified by the peak area ratio of D0A0 (HS), D0S0 (HS) and D0a4 (DS/CS) to the internal standard using MultiQuant 3.0.2 (Sciex). Reported GAG amounts were normalized to total protein levels as measured by a BCA assay (Pierce). Fold over TfR$^{mu/hu}$ KI values were calculated as follows:

$$= \frac{\text{Average GAG level of each group}}{\text{Average } GAG \text{ level of } TfR \ KI \text{ vehicle treated group}}$$

Percent reduction from vehicle treated Ids KO; TfR$^{mu/hu}$ KI mice were calculated as follows:

$$= 100 \times \frac{\begin{array}{c}(\text{Average } GAG \text{ level of vehicle treated } Ids \ KO; \\ TfR \ KI \text{ group} - \text{Average } GAG \text{ level for each treatment group})\end{array}}{\text{Average } GAG \text{ level of } Ids \ KO; TfR \ KI \text{ vehicle treated group}}$$

Heparan Sulfate (HS) and Dermatan Sulfate (DS) Calibration Curves

Pure standards for D0a4 (DS/CS), DaA0 (HS), and D0S0 (HS) were dissolved in acetonitrile:water 50/50 (v/v) to generate a 1 mg/mL stock. An 8-point dilution curve in PBS was generated ranging from 0.12 ng to 1000 ng. Subsequently, the internal standard D4UA-2S-GlcNCOEt-6S (20 ng) was added to each serial dilution. Samples were then boiled for 10 minutes at 95° C. and then spun to pellet any particulate matter. Supernatant was filtered using a 30 kD MWCO cellulose acetate filter plate (Millipore, MSUN03010) by spinning at 3364×g for 5 minutes at room temperature. Resulting flow through was mixed with an equal part of acetonitrile in glass vials and run by mass spectrometry as described above.

Results

Figure 4:
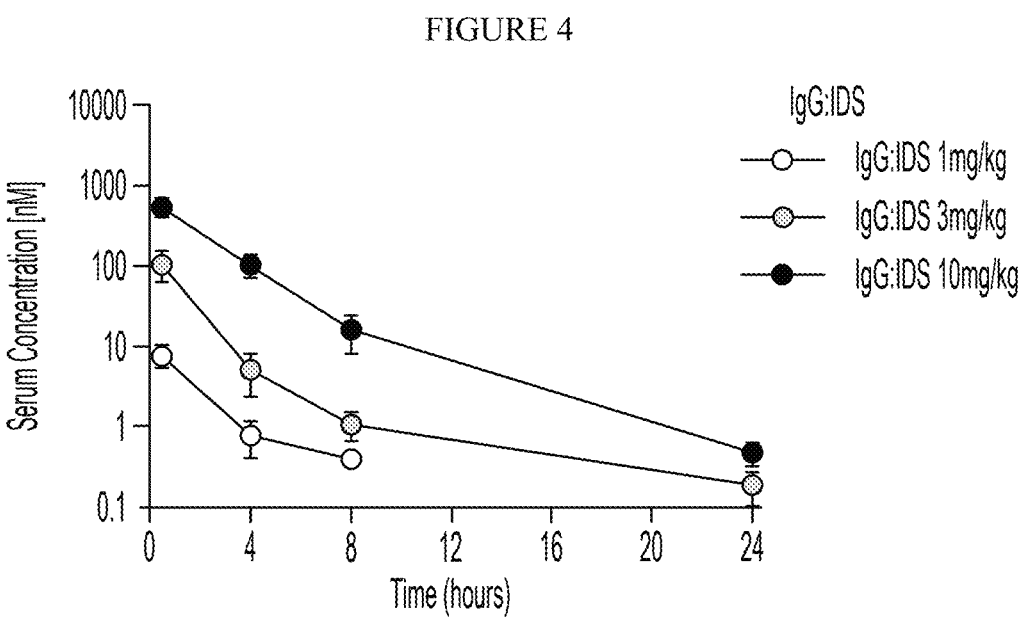
FIG. 4 shows the pharmacokinetic (PK) profile of IgG:IDS in the serum of $TfR^{mu/hu}$ KI mice (n=3 per group), which received a single intravenous dose of IgG:IDS at 1, 3, or 10 mg/kg. Terminal samples were collected at 0.5, 4, 8, and 24 hours post dose.
Figure 5:
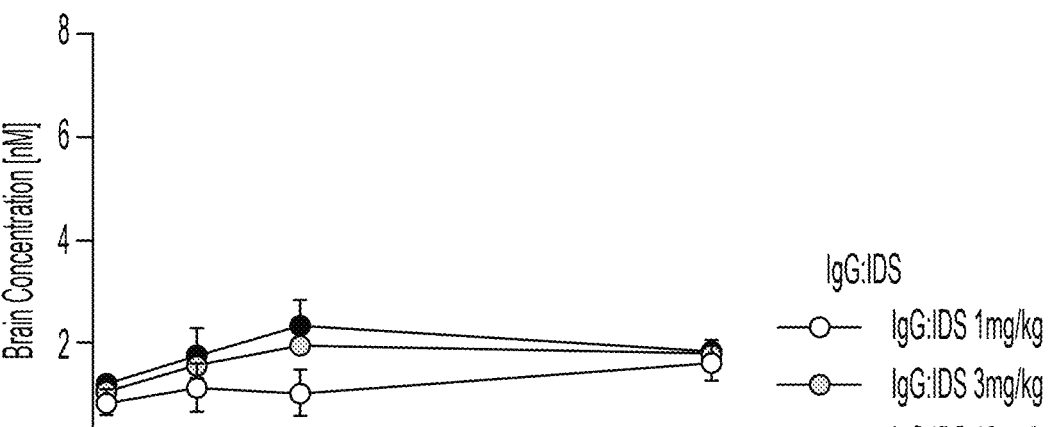
FIG. 5 shows the PK profile of IgG:IDS in the brain of $TfR^{mu/hu}$ KI mice (n=3 per group), which received a single intravenous dose of IgG:IDS at 1, 3, or 10 mg/kg. Terminal samples were collected at 0.5, 4, 8, and 24 hours post dose.
Figure 6:
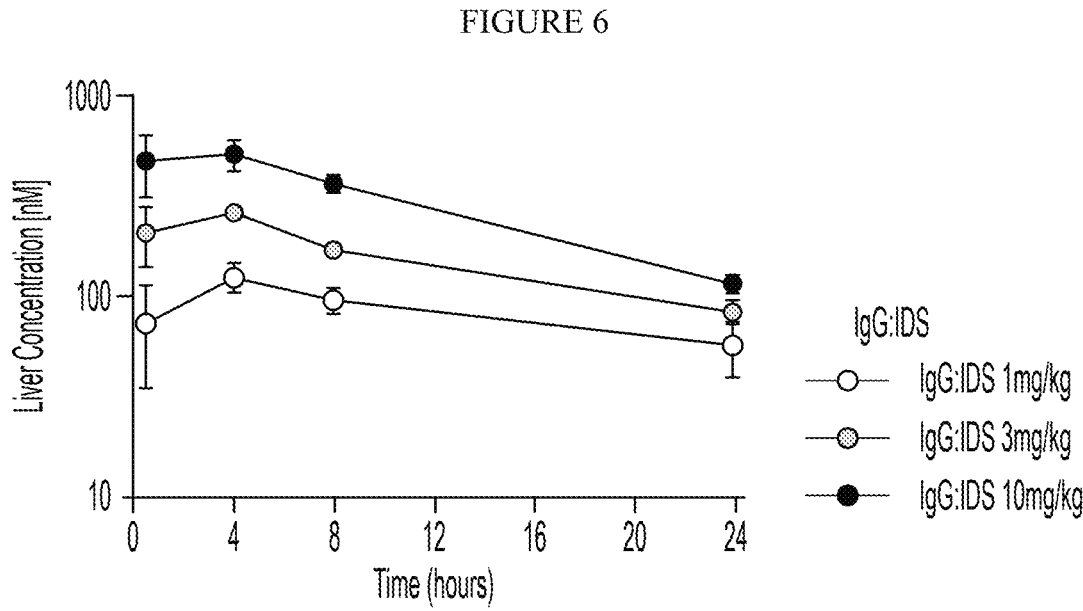
FIG. 6 shows the PK profile of IgG:IDS in the liver of $TfR^{mu/hu}$ KI mice (n=3 per group), which received a single intravenous dose of IgG:IDS at 1, 3, or 10 mg/kg. Terminal samples were collected at 0.5, 4, 8, and 24 hours post dose.

Pharmacokinetic profiles of IgG:IDS are illustrated in FIGS. 4-6. Serum exposures of IgG:IDS are illustrated in FIG. 4 and exhibit a dose-dependent effect. IgG:IDS brain PK profiles are illustrated in FIG. 5; maximal concentrations were observed at 4-8 hours post-dose. IgG:IDS liver PK levels are illustrated in FIG. 6; IgG:IDS exhibited good liver uptake.

Figure 7A:
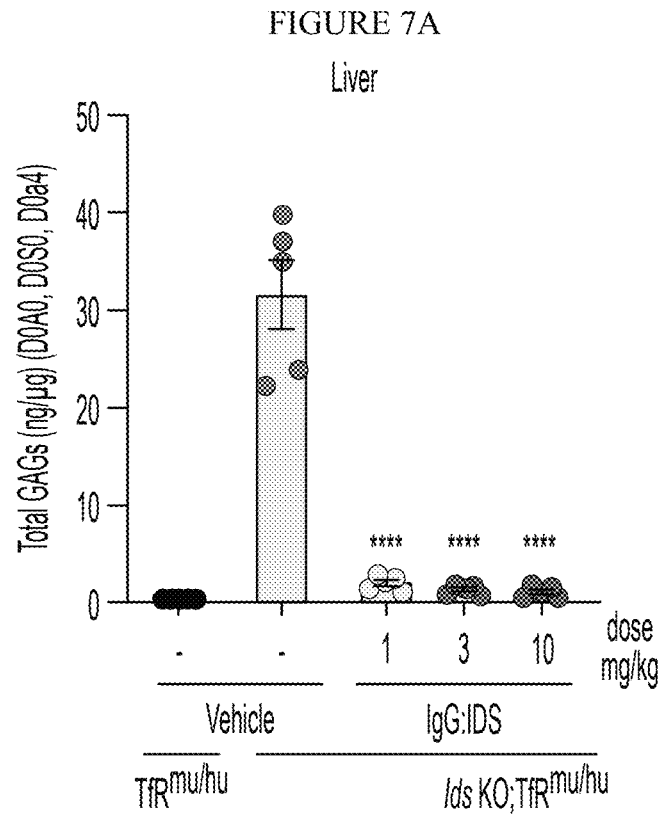
FIGS. 7A-7C show total GAG levels (A) heparan sulfate (HS) levels (B) and dermatan sulfate (DS) levels (C) in liver from Ids KO; $TfR^{mu/hu}$ KI mice, which had been administered a single intravenous dose of 1, 3, or 10 mg/kg of IgG:IDS (n=5 per group). GAG levels were measured 7 days post dose and compared to vehicle treatment and $TfR^{mu/hu}$ KI mice; n=5 per group. Graphs display mean±SEM and p values: one-way ANOVA with Tukey's multiple comparison test; **** p<0.0001.
Figure 7B:
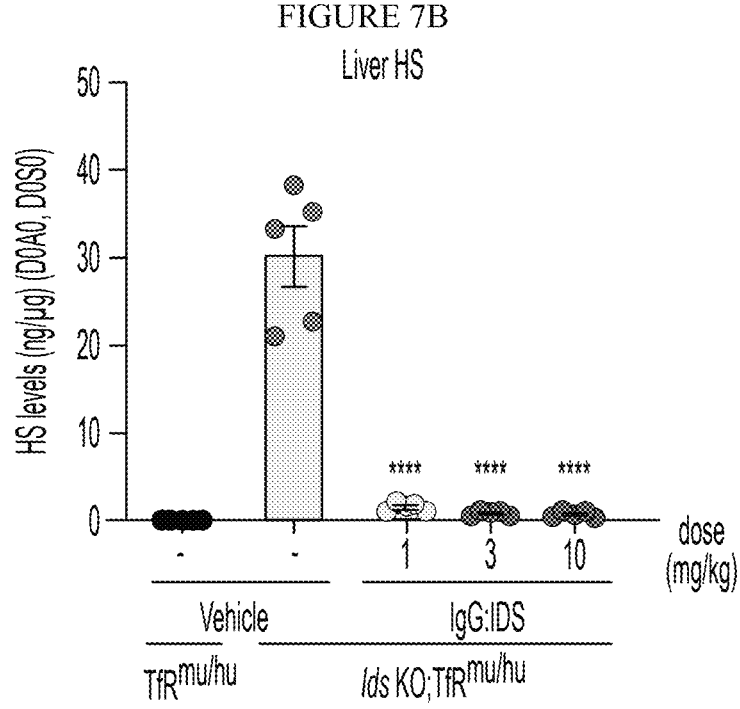
Figure 7C:
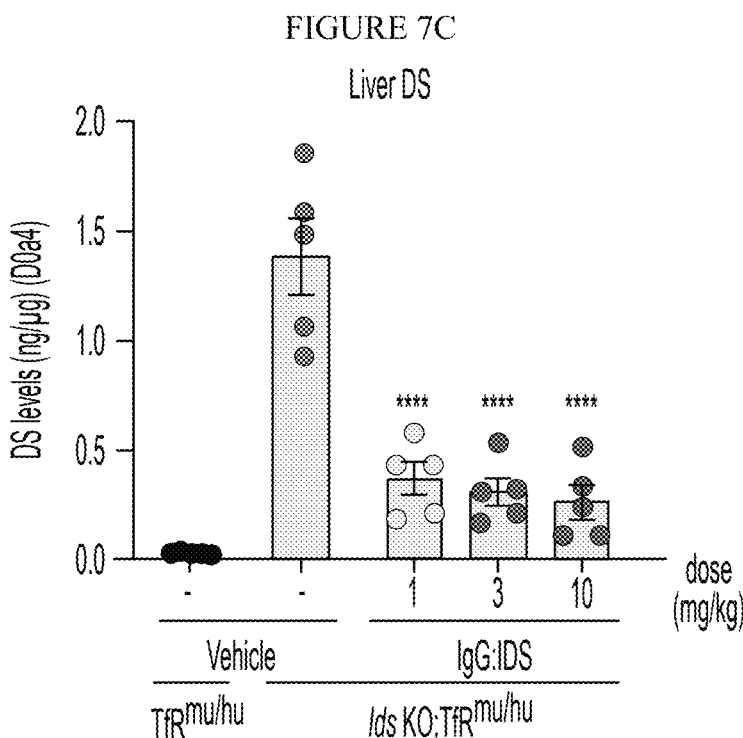
Figure 8A:
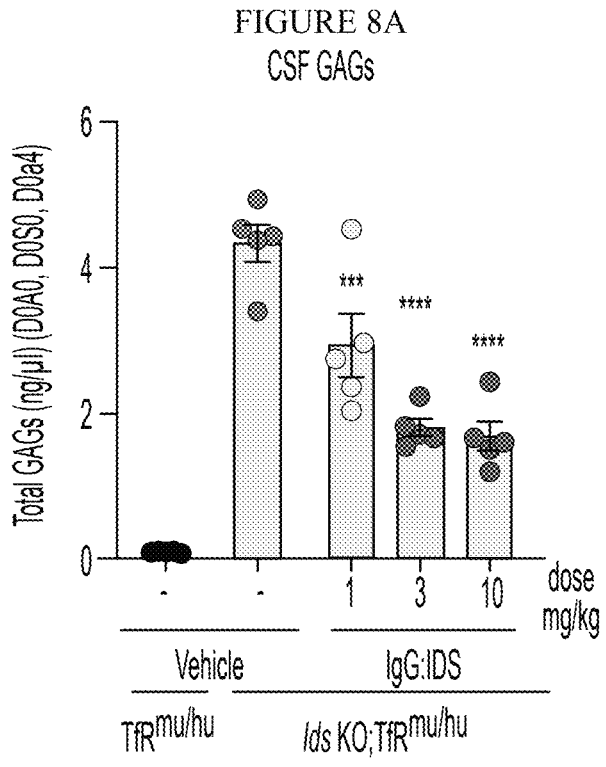
FIGS. 8A-8C show total GAG levels (A) heparan sulfate (HS) levels (B) and dermatan sulfate (DS) levels (C) in CSF from Ids KO; $TfR^{mu/hu}$ KI mice, which had been administered a single intravenous dose of 1, 3, or 10 mg/kg of IgG:IDS (n=5 per group). GAG levels were measured 7 days post dose and compared to vehicle treatment and $TfR^{mu/hu}$ KI mice; n=5 per group. Graphs display mean±SEM and p values: one-way ANOVA with Tukey's multiple comparison test;  p<0.01; * p<0.001; and **** p<0.0001.
Figure 8B:
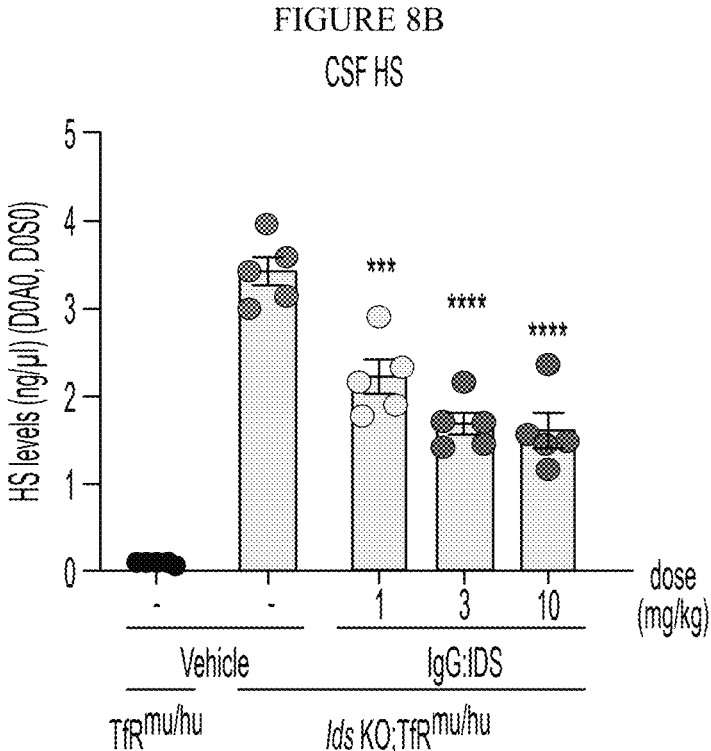
Figure 8C:
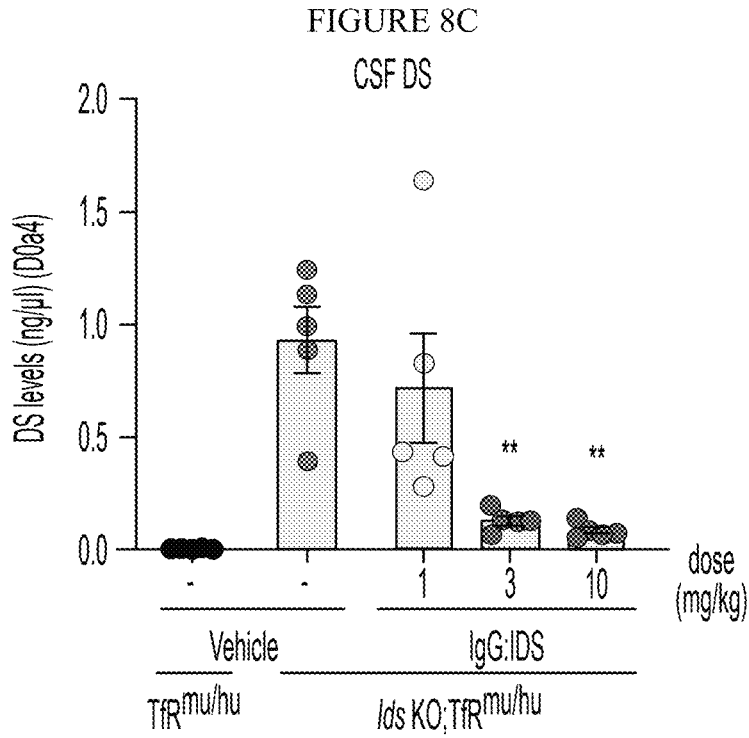
Figure 9A:
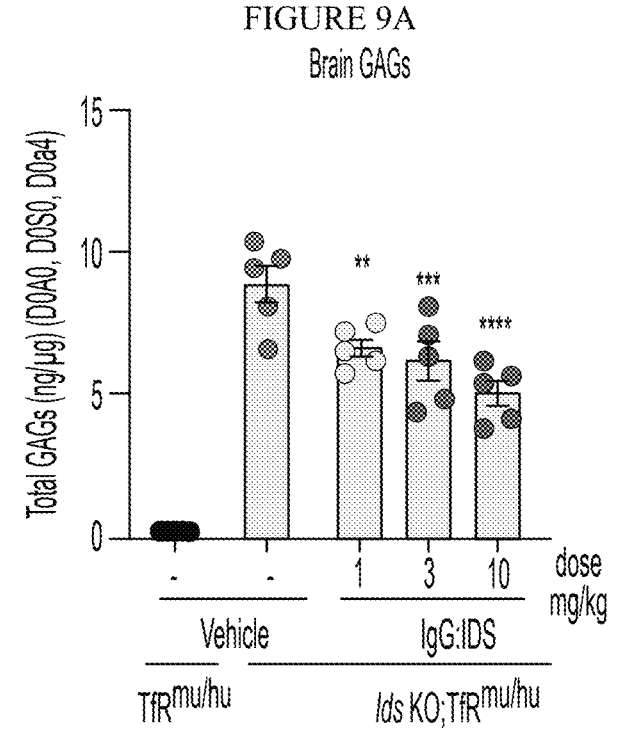
FIGS. 9A-9C show total GAG levels (A) heparan sulfate (HS) levels (B) and dermatan sulfate (DS) levels (C) in brain from Ids KO; $TfR^{mu/hu}$ KI mice, which had been administered a single intravenous dose of 1, 3, or 10 mg/kg of IgG:IDS (n=5 per group). GAG levels were measured 7 days post dose and compared to vehicle treatment and TfR$^{mu/hu}$ KI mice (n=5 per group). Graphs display mean±SEM and p values: one-way ANOVA with Tukey's multiple comparison test; * p<0.05;  p<0.01; * p<0.001; and **** p<0.0001.
Figure 9B:
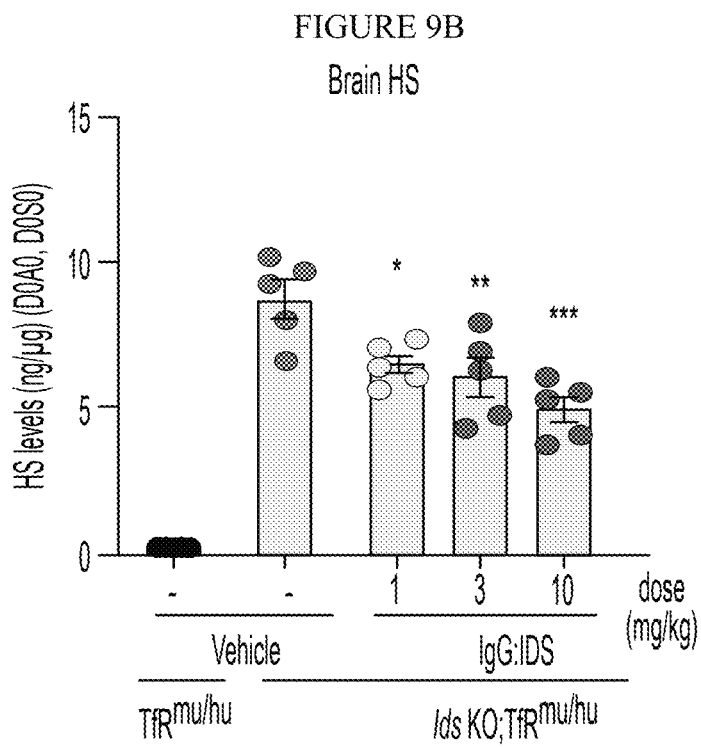
Figure 9C:
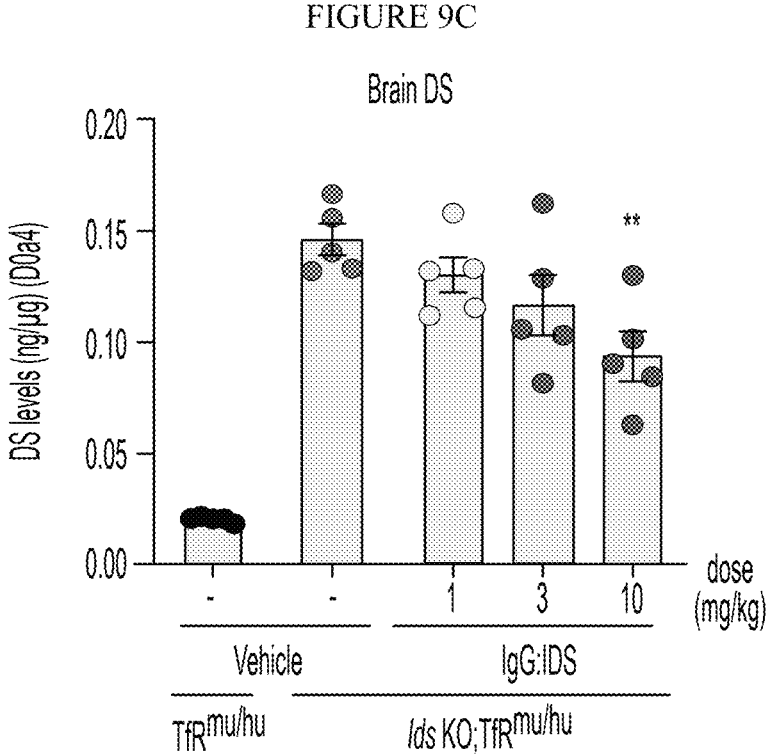

To investigate pharmacodynamic effects, TfR$^{mu/hu}$ KI mice received a single intravenous dose of IgG:IDS at 1, 3, or 10 mg/kg, and GAG levels (total GAG levels; HS levels; and DS levels) in liver, CSF, and brain were assessed after seven days (see, FIGS. 7-9). The fold over TfR$^{mu/hu}$ KI total GAG levels in the liver, CSF and brain are presented in Table 2. The percent reduction from Ids KO; TfR$^{mu/hu}$ KI+vehicle total GAG levels in the liver, CSF and brain are shown in Table 3. The percent reduction from Ids KO; TfR$^{mu/hu}$ KI+vehicle HS and DS levels in the liver, CSF and brain are shown in Tables 4 and 5, respectively.

TABLE 3

Percent reduction from Ids KO; TfR$^{mu/hu}$ KI + vehicle Total GAG levels.

| Dose (mg/kg) | Liver | CSF | Brain |
|---|---|---|---|
| 1 | 93.9 | 32.4 | 24.7 |
| 3 | 96.0 | 58.3 | 30.4 |
| 10 | 96.8 | 61.0 | 42.7 |

TABLE 4

Percent reduction from Ids KO; TfR$^{mu/hu}$ KI + vehicle HS (D0A0, D0S0) levels.

| Dose (mg/kg) | Liver | CSF | Brain |
|---|---|---|---|
| 1 | 94.9 | 35.1 | 24.9 |
| 3 | 96.9 | 50.9 | 30.5 |
| 10 | 97.5 | 52.9 | 42.8 |

TABLE 2

Fold over TfR$^{mu/hu}$ KI Total GAG levels.

| Dose (mg/kg) | Liver | CSF | Brain |
|---|---|---|---|
| 0 | 161.3 | 44.1 | 29.7 |
| 1 | 9.8 | 29.8 | 22.3 |
| 3 | 6.4 | 18.4 | 20.6 |
| 10 | 5.2 | 17.2 | 17.0 |

TABLE 5

Percent reduction from Ids KO; TfR$^{mu/hu}$ KI + vehicle DS (D0a4) levels.

| Dose (mg/kg) | Liver | CSF | Brain |
|---|---|---|---|
| 1 | 73.5 | 22.5 | 10.7 |
| 3 | 77.7 | 85.8 | 20.4 |
| 10 | 80.9 | 91.0 | 35.9 |

TABLE 6

Informal Sequence Listing

| SEQ ID NO: | Sequence | Description |
|---|---|---|
| 1 | MPPPRTGRGLLWLGLVLSSVCVALGSETQANSTTDALNVLLIIV DDLRPSLGCYGDKLVRSPNIDQLASHSLLFQNAFAQQAVCAPSR VSFLTGRRPDTTRLYDENSYWRVHAGNFSTIPQYFKENGYVTMS VGKVFHPGISSNHTDDSPYSWSFPPYHPSSEKYENTKTCRGPDG ELHANLLCPVDVLDVPEGTLPDKQSTEQAIQLLEKMKTSASPFF LAVGYHKPHIPFRYPKEFQKLYPLENITLAPDPEVPDGLPPVAY NPWMDIRQREDVQALNISVPYGPIPVDFQRKIRQSYFASVSYLD TQVGRLLSALDDLQLANSTIIAFTSDHGWALGEHGEWAKYSNED VATHVPLIFYVPGRTASLPEAGEKLFPYLDPFDSASQLMEPGRQ SMDLVELVSLFPTLAGLAGLQVPPRCPVPSFHVELCREGKNLLK HFRFRDLEEDPYLPGNPRELIAYSQYPRPSDIPQWNSDKPSLKD IKIMGYSIRTIDYRYTVWVGFNPDEFLANFSDIHAGELYFVDSD PLQDHNMYNDSQGGDLFQLLMP | Full-length human IDS polypeptide sequence |
| 2 | TDALNVLLIIVDDLRPSLGCYGDKLVRSPNIDQLASHSLLFQNA FAQQAVCAPSRVSFLTGRRPDTTRLYDENSYWRVHAGNESTIPQ YFKENGYVTMSVGKVFHPGISSNHTDDSPYSWSFPPYHPSSEKY ENTKTCRGPDGELHANLLCPVDVLDVPEGTLPDKQSTEQAIQLL EKMKTSASPFFLAVGYHKPHIPFRYPKEFQKLYPLENITLAPDP EVPDGLPPVAYNPWMDIRQREDVQALNISVPYGPIPVDFQRKIR QSYFASVSYLDTQVGRLLSALDDLQLANSTIIAFTSDHGWALGE HGEWAKYSNFDVATHVPLIFYVPGRTASLPEAGEKLFPYLDPFD SASQLMEPGRQSMDLVELVSLEPTLAGLAGLQVPPRCPVPSFHV ELCREGKNLLKHFRFRDLEEDPYLPGNPRELIAYSQYPRPSDIP QWNSDKPSLKDIKIMGYSIRTIDYRYTVWVGENPDEFLANFSDI HAGELYFVDSDPLQDHNMYNDSQGGDLFQLLMP | Mature human IDS polypeptide sequence |
| 3 | SETQANSTTDALNVLLIIVDDLRPSLGCYGDKLVRSPNIDQLAS HSLLFQNAFAQQAVCAPSRVSFLTGRRPDTTRLYDENSYWRVHA GNFSTIPQYFKENGYVTMSVGKVFHPGISSNHTDDSPYSWSFPP YHPSSEKYENTKTCRGPDGELHANLLCPVDVLDVPEGTLPDKQS TEQAIQLLEKMKTSASPFFLAVGYHKPHIPFRYPKEFQKLYPLE NITLAPDPEVPDGLPPVAYNPWMDIRQREDVQALNISVPYGPIP VDFQRKIRQSYFASVSYLDTQVGRLLSALDDLQLANSTIIAFTS DHGWALGEHGEWAKYSNEDVATHVPLIFYVPGRTASLPEAGEKL | IDS sequence |

TABLE 6-continued

| | Informal Sequence Listing | |
|---|---|---|
| SEQ ID NO: | Sequence | Description |
| | FPYLDPFDSASQLMEPGRQSMDLVELVSLFPTLAGLAGLQVPPR CPVPSFHVELCREGKNLLKHFRFRDLEEDPYLPGNPRELIAYSQ YPRPSDIPQWNSDKPSLKDIKIMGYSIRTIDYRYTVWVGFNPDE FLANFSDIHAGELYFVDSDPLQDHNMYNDSQGGDLFQLLMP | |
| 4 | SETQANSTTDALNVLLIIVDDLRPSLGCYGDKLVRSPNIDQLAS HSLLFQNAFAQQAV<u>fG</u>APSRVSFLTGRRPDTTRLYDENSYWRVH AGNFSTIPQYFKENGYVTMSVGKVFHPGISSNHTDDSPYSWSFP PYHPSSEKYENTKTCRGPDGELHANLLCPVDVLDVPEGTLPDKQ STEQAIQLLEKMKTSASPFFLAVGYHKPHIPFRYPKEFQKLYPL ENITLAPDPEVPDGLPPVAYNPWMDIRQREDVQALNISVPYGPI PVDFQRKIRQSYFASVSYLDTQVGRLLSALDDLQLANSTIIAFT SDHGWALGEHGEWAKYSNFDVATHVPLIFYVPGRTASLPEAGEK LFPYLDPFDSASQLMEPGRQSMDLVELVSLEPTLAGLAGLQVPP RCPVPSFHVELCREGKNLLKHFRFRDLEEDPYLPGNPRELIAYS QYPRPSDIPQWNSDKPSLKDIKIMGYSIRTIDYRYTVWVGFNPD EFLANFSDIHAGELYFVDSDPLQDHNMYNDSQGGDLFQLLMP | IDS sequence (formylglycine residue "fG" double underlined) |
| 5 | DIVMTQTPLSLSVTPGQPASISCRSSQSLVHSNGNTYLHW YLQKPGQSPQLLIYKVSNRFSGVPDRESGSGSGTDETLKI SRVEAEDVGVYYCSQSTHVPWTFGQGTKVEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSENRGEC | Light chain of anti-TfR antibody embodiment |
| 6 | DIVMTQTPLSLSVTPGQPASISCRSSQSLVHSNGNTYLHW YLQKPGQSPQLLIYKVSNRFSGVPDRFSGSGSGTDFTLKI SRVEAEDVGVYYCSQSTHVPWTFGQGTKVEIK | Light chain variable region sequence of anti- TfR antibody embodiment |
| 7 | RSSQSLVHSNGNTYLH | CDR-L1 |
| 8 | KVSNRFS | CDR-L2 |
| 9 | SQSTHVPWT | CDR-L3 |
| 10 | EVQLVQSGAEVKKPGESLKISCKGSGYSFTNYWLGWVRQM PGKGLEWMGDIYPGGDYPTYSEKFKVQVTISADKSISTAY LQWSSLKASDTAMYYCARSGNYDEVAYWGQGTLVTVSSAS TKGPSVFPLAPSSKSTSGGTAALGCLVKDYFPEPVTVSWN SGALTSGVHTFPAVLQSSGLYSLSSVVTVPSSSLGTQTYI CNVNHKPSNTKVDKKVEPKSCDKTHTCPPCPAPELLGGPS VFLFPPKPKDTLMISRTPEVTCVVVDVSHEDPEVKENWYV DGVEVHNAKTKPREEQYNSTYRVVSVLTVLHQDWLNGKEY KCKVSNKALPAPIEKTISKAKGQPREPQVYTLPPSRDELT KNQVSLTCLVKGFYPSDIAVEWESNGQPENNYKTTPPVLD SDGSFFLYSKLTVDKSRWQQGNVFSCSVMHEALHNHYTQK SLSLSPGK | Heavy chain of anti-TfR antibody embodiment |
| 11 | EVQLVQSGAEVKKPGESLKISCKGSGYSFTNYWLGWVRQM PGKGLEWMGDIYPGGDYPTYSEKFKVQVTISADKSISTAY LQWSSLKASDTAMYYCARSGNYDEVAYWGQGTLVTVSS | Heavy chain variable region sequence of anti- TfR antibody embodiment |
| 12 | GYSF$X_1$NY | CDR-H1, wherein $X_1$ is M or T |
| 13 | GYSFTNY | CDR-H1 embodiment 1 |
| 14 | GYSFMNY | CDR-H1 embodiment 2 |
| 15 | YPGGDY | CDR-H2 |
| 16 | SGNYDEVAY | CDR-H3 |
| 17 | EVQLVQSGAEVKKPGESLKISCKGSGYSFTNYWLGWVRQMPGKG LEWMGDIYPGGDYPTYSEKFKVQVTISADKSISTAYLQWSSLKA SDTAMYYCARSGNYDEVAYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKKVEPKS CDKTHTCPPCPAPELLGGPSVFLFPPKPKDTLMISRTPEVTCVV VDVSHEDPEVKFNWYVDGVEVHNAKTKPREEQYNSTYRVVSVLT VLHQDWLNGKEYKCKVSNKALPAPIEKTISKAKGQPREPQVYTL PPSRDELTKNQVSLTCLVKGFYPSDIAVEWESNGQPENNYKTTP PVLDSDGSFFLYSKLTVDKSRWQQGNVFSCSVMHEALHNHYTQK SLSLSPGKGSSETQANSTTDALNVLLIIVDDLRPSLGCYGDKLV RSPNIDQLASHSLLFQNAFAQQAVCAPSRVSFLTGRRPDTTRLY | Fusion polypeptide comprising heavy chain and IDS sequence |

TABLE 6-continued

Informal Sequence Listing

| SEQ ID NO: | Sequence | Description |
|---|---|---|
| | DENSYWRVHAGNFSTIPQYFKENGYVTMSVGKVFHPGISSNHTD DSPYSWSFPPYHPSSEKYENTKTCRGPDGELHANLLCPVDVLDV PEGTLPDKQSTEQAIQLLEKMKTSASPFFLAVGYHKPHIPFRYP KEFQKLYPLENITLAPDPEVPDGLPPVAYNPWMDIRQREDVQAL NISVPYGPIPVDFQRKIRQSYFASVSYLDTQVGRLLSALDDLQL ANSTIIAFTSDHGWALGEHGEWAKYSNFDVATHVPLIFYVPGRT ASLPEAGEKLFPYLDPFDSASQLMEPGRQSMDLVELVSLEPTLA GLAGLQVPPRCPVPSFHVELCREGKNLLKHFRFRDLEEDPYLPG NPRELIAYSQYPRPSDIPQWNSDKPSLKDIKIMGYSIRTIDYRY TVWVGFNPDEFLANFSDIHAGELYFVDSDPLQDHNMYNDSQGGD LFQLLMP | |
| 18 | EVQLVQSGAEVKKPGESLKISCKGSGYSFTNYWLGWVRQMPGKG LEWMGDIYPGGDYPTYSEKFKVQVTISADKSISTAYLQWSSLKA SDTAMYYCARSGNYDEVAYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKKVEPKS CDKTHTCPPCPAPELLGGPSVFLFPPKPKDTLMISRTPEVTCVV VDVSHEDPEVKFNWYVDGVEVHNAKTKPREEQYNSTYRVVSVLT VLHQDWLNGKEYKCKVSNKALPAPIEKTISKAKGQPREPQVYTL PPSRDELTKNQVSLTCLVKGFYPSDIAVEWESNGQPENNYKTTP PVLDSDGSFFLYSKLTVDKSRWQQGNVFSCSVMHEALHNHYTQK SLSLSPGKGSSETQANSTTDALNVLLIIVDDLRPSLGCYGDKLV RSPNIDQLASHSLLFQNAFAQQAV<u>fG</u>APSRVSFLTGRRPDTTRL YDFNSYWRVHAGNFSTIPQYFKENGYVTMSVGKVFHPGISSNHT DDSPYSWSFPPYHPSSEKYENTKTCRGPDGELHANLLCPVDVLD VPEGTLPDKQSTEQAIQLLEKMKTSASPFFLAVGYHKPHIPFRY PKEFQKLYPLENITLAPDPEVPDGLPPVAYNPWMDIRQREDVQA LNISVPYGPIPVDFQRKIRQSYFASVSYLDTQVGRLLSALDDLQ LANSTIIAFTSDHGWALGEHGEWAKYSNFDVATHVPLIFYVPGR TASLPEAGEKLFPYLDPFDSASQLMEPGRQSMDLVELVSLFPTL AGLAGLQVPPRCPVPSFHVELCREGKNLLKHFRFRDLEEDPYLP GNPRELIAYSQYPRPSDIPQWNSDKPSLKDIKIMGYSIRTIDYR YTVWVGFNPDEFLANFSDIHAGELYFVDSDPLQDHNMYNDSQGG DLFQLLMP | Fusion polypeptide comprising heavy chain and IDS sequence (formylglycine residue "fG" double underlined) |
| 19 | GGGGS | Linker Embodiment 1 |
| 20 | GGGGGS | Linker Embodiment 2 |
| 21 | SGGGG | Linker Embodiment 3 |
| 22 | GGS | Linker Embodiment 4 |
| 23 | GS | Linker Embodiment 5 |
| 24 | APELLGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPAPIEKTISKAKGQPREPQVYTLPPSRDELTKNQ VSLTCLVKGFYPSDIAVEWESNGQPENNYKTTPPVLDSDGSFFL YSKLTVDKSRWQQGNVFSCSVMHEALHNHYTQKSLSLSPGK | Wild-type human Fc sequence positions 231-447 EU index numbering |
| 25 | EPKSCDKTHTCPPCP | Human IgG1 hinge amino acid sequence |
| 26 | MMDQARSAFSNLFGGEPLSYTRESLARQVDGDNSHVEMKLAVDE EENADNNTKANVTKPKRCSGSICYGTIAVIVFFLIGFMIGYLGY CKGVEPKTECERLAGTESPVREEPGEDFPAARRLYWDDLKRKLS EKLDSTDFTGTIKLLNENSYVPREAGSQKDENLALYVENQFREF KLSKVWRDQHFVKIQVKDSAQNSVIIVDKNGRLVYLVENPGGYV AYSKAATVTGKLVHANFGTKKDFEDLYTPVNGSIVIVRAGKITF AEKVANAESLNAIGVLIYMDQTKFPIVNAELSFFGHAHLGTGDP YTPGFPSFNHTQFPPSRSSGLPNIPVQTISRAAAEKLEGNMEGD CPSDWKTDSTCRMVTSESKNVKLTVSNVLKEIKILNIFGVIKGF VEPDHYVVVGAQRDAWGPGAAKSGVGTALLLKLAQMESDMVLKD GFQPSRSIIFASWSAGDFGSVGATEWLEGYLSSLHLKAFTYINL DKAVLGTSNFKVSASPLLYTLIEKTMQNVKHPVTGQFLYQDSNW ASKVEKLTLDNAAFPFLAYSGIPAVSFCFCEDTDYPYLGTTMDT YKELIERIPELNKVARAAAEVAGQFVIKLTHDVELNLDYERYNS QLLSFVRDLNQYRADIKEMGLSLQWLYSARGDFFRATSRLTTDE GNAEKTDRFVMKKLNDRVMRVEYHFLSPYVSPKESPFRHVEWGS GSHTLPALLENLKLRKQNNGAFNETLFRNQLALATWTIQGAANA LSGDVWDIDNEF | Human transferrin receptor protein 1 (TFR1) |

TABLE 6-continued

Informal Sequence Listing

| SEQ ID NO: | Sequence | Description |
|---|---|---|
| 27 | NSVIIVDKNGRLVYLVENPGGYVAYSKAATVTGKLVHANFGTKK DFEDLYTPVNGSIVIVRAGKITFAEKVANAESLNAIGVLIYMDQ TKFPIVNAELSFFGHAHLGTGDPYTPGFPSFNHTQFPPSRSSGL PNIPVQTISRAAAEKLEGNMEGDCPSDWKTDSTCRMVTSESKNV KLTVS | Human TfR apical domain |

All publications, patents, and patent documents are incorporated by reference herein, as though individually incorporated by reference. The present disclosure has been 15 described with reference to various specific and preferred embodiments and techniques. However, it should be understood that many variations and modifications may be made while remaining within the spirit and scope of the invention.

SEQUENCE LISTING

Sequence total quantity: 27
SEQ ID NO: 1              moltype = AA  length = 550
FEATURE                   Location/Qualifiers
source                    1..550
                          mol_type = protein
                          organism = Homo sapiens
SEQUENCE: 1
MPPPRTGRGL LWLGLVLSSV CVALGSETQA NSTTDALNVL LIIVDDLRPS LGCYGDKLVR   60
SPNIDQLASH SLLFQNAFAQ QAVCAPSRVS FLTGRRPDTT RLYDFNSYWR VHAGNFSTIP  120
QYFKENGYVT MSVGKVFHPG ISSNHTDDSP YSWSFPPYHP SSEKYENTKT CRGPDGELHA  180
NLLCPVDVLD VPEGTLPDKQ STEQAIQLLE KMKTSASPFF LAVGYHKPHI PFRYPKEFQK  240
LYPLENITLA PDPEVPDGLP PVAYNPWMDI RQREDVQALN ISVPYGPIPV DFQRKIRQSY  300
FASVSYLDTQ VGRLLSALDD LQLANSTIIA FTSDHGWALG EHGEWAKYSN FDVATHVPLI  360
FYVPGRTASL PEAGEKLFPY LDPFDSASQL MEPGRQSMDL VELVSLFPTL AGLAGLQVPP  420
RCPVPSFHVE LCREGKNLLK HFRFRDLEED PYLPGNPREL IAYSQYPRPS DIPQWNSDKP  480
SLKDIKIMGY SIRTIDYRYT VWVGFNPDEF LANFSDIHAG ELYFVDSDPL QDHNMYNDSQ  540
GGDLFQLLMP                                                        550

SEQ ID NO: 2              moltype = AA  length = 517
FEATURE                   Location/Qualifiers
source                    1..517
                          mol_type = protein
                          organism = Homo sapiens
SEQUENCE: 2
TDALNVLLII VDDLRPSLGC YGDKLVRSPN IDQLASHSLL FQNAFAQQAV CAPSRVSFLT   60
GRRPDTTRLY DFNSYWRVHA GNFSTIPQYF KENGYVTMSV GKVFHPGISS NHTDDSPYSW  120
SFPPYHPSSE KYENTKTCRG PDGELHANLL CPVDVLDVPE GTLPDKQSTE QAIQLLEKMK  180
TSASPFFLAV GYHKPHIPFR YPKEFQKLYP LENITLAPDP EVPDGLPPVA YNPWMDIRQR  240
EDVQALNISV PYGPIPVDFQ RKIRQSYFAS VSYLDTQVGR LLSALDDLQL ANSTIIAFTS  300
DHGWALGEHG EWAKYSNFDV ATHVPLIFYV PGRTASLPEA GEKLFPYLDP FDSASQLMEP  360
GRQSMDLVEL VSLFPTLAGL AGLQVPPRCP VPSFHVELCR EGKNLLKHFR FRDLEEDPYL  420
PGNPRELIAY SQYPRPSDIP QWNSDKPSLK DIKIMGYSIR TIDYRYTVWV GFNPDEFLAN  480
FSDIHAGELY FVDSDPLQDH NMYNDSQGGD LFQLLMP                          517

SEQ ID NO: 3              moltype = AA  length = 525
FEATURE                   Location/Qualifiers
source                    1..525
                          mol_type = protein
                          organism = Homo sapiens
SEQUENCE: 3
SETQANSTTD ALNVLLIIVD DLRPSLGCYG DKLVRSPNID QLASHSLLFQ NAFAQQAVCA   60
PSRVSFLTGR RPDTTRLYDF NSYWRVHAGN FSTIPQYFKE NGYVTMSVGK VFHPGISSNH  120
TDDSPYSWSF PPYHPSSEKY ENTKTCRGPD GELHANLLCP VDVLDVPEGT LPDKQSTEQA  180
IQLLEKMKTS ASPFFLAVGY HKPHIPFRYP KEFQKLYPLE NITLAPDPEV PDGLPPVAYN  240
PWMDIRQRED VQALNISVPY GPIPVDFQRK IRQSYFASVS YLDTQVGRLL SALDDLQLAN  300
STIIAFTSDH GWALGEHGEW AKYSNFDVAT HVPLIFYVPG RTASLPEAGE KLFPYLDPFD  360
SASQLMEPGR QSMDLVELVS LFPTLAGLAG LQVPPRCPVP SFHVELCREG KNLLKHFRFR  420
DLEEDPYLPG NPRELIAYSQ YPRPSDIPQW NSDKPSLKDI KIMGYSIRTI DYRYTVWVGF  480
NPDEFLANFS DIHAGELYFV DSDPLQDHNM YNDSQGGDLF QLLMP                 525

SEQ ID NO: 4              moltype = AA  length = 525
FEATURE                   Location/Qualifiers
REGION                    1..525

-continued

```
                        note = Description of Artificial Sequence: Synthetic
                         polypeptide
SITE                    59
                        note = Formylglycine
source                  1..525
                        mol_type = protein
                        organism = synthetic construct
SEQUENCE: 4
SETQANSTTD ALNVLLIIVD DLRPSLGCYG DKLVRSPNID QLASHSLLFQ NAFAQQAVGA  60
PSRVSFLTGR RPDTTRLYDF NSYWRVHAGN FSTIPQYFKE NGYVTMSVGK VFHPGISSNH  120
TDDSPYSWSF PPYHPSSEKY ENTKTCRGPD GELHANLLCP VDVLDVPEGT LPDKQSTEQA  180
IQLLEKMKTS ASPFFLAVGY HKPHIPFRYP KEFQKLYPLE NITLAPDPEV PDGLPPVAYN  240
PWMDIRQRED VQALNISVPY GPIPVDFQRK IRQSYFASVS YLDTQVGRLL SALDDLQLAN  300
STIIAFTSDH GWALGEHGEW AKYSNFDVAT HVPLIFYVPG RTASLPEAGE KLFPYLDPFD  360
SASQLMEPGR QSMDLVELVS LFPTLAGLAG LQVPPRCPVP SFHVELCREG KNLLKHFRFR  420
DLEEDPYLPG NPRELIAYSQ YPRPSDIPQW NSDKPSLKDI KIMGYSIRTI DYRYTVWVGF  480
NPDEFLANFS DIHAGELYFV DSDPLQDHNM YNDSQGGDLF QLLMP              525

SEQ ID NO: 5            moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 5
DIVMTQTPLS LSVTPGQPAS ISCRSSQSLV HSNGNTYLHW YLQKPGQSPQ LLIYKVSNRF  60
SGVPDRFSGS GSGTDFTLKI SRVEAEDVGV YYCSQSTHVP WTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 6            moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 6
DIVMTQTPLS LSVTPGQPAS ISCRSSQSLV HSNGNTYLHW YLQKPGQSPQ LLIYKVSNRF  60
SGVPDRFSGS GSGTDFTLKI SRVEAEDVGV YYCSQSTHVP WTFGQGTKVE IK          112

SEQ ID NO: 7            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 7
RSSQSLVHSN GNTYLH                                                16

SEQ ID NO: 8            moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 8
KVSNRFS                                                          7

SEQ ID NO: 9            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 9
SQSTHVPWT                                                        9

SEQ ID NO: 10           moltype = AA  length = 448
FEATURE                 Location/Qualifiers
REGION                  1..448
                        note = Description of Artificial Sequence: Synthetic
                         polypeptide
```

-continued

```
source                   1..448
                         mol_type = protein
                         organism = synthetic construct
SEQUENCE: 10
EVQLVQSGAE VKKPGESLKI SCKGSGYSFT NYWLGWVRQM PGKGLEWMGD IYPGGDYPTY  60
SEKFKVQVTI SADKSISTAY LQWSSLKASD TAMYYCARSG NYDEVAYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 11           moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 11
EVQLVQSGAE VKKPGESLKI SCKGSGYSFT NYWLGWVRQM PGKGLEWMGD IYPGGDYPTY  60
SEKFKVQVTI SADKSISTAY LQWSSLKASD TAMYYCARSG NYDEVAYWGQ GTLVTVSS    118

SEQ ID NO: 12           moltype = AA  length = 7
FEATURE                 Location/Qualifiers
REGION                  1..7
                        note = Description of Artificial Sequence: Synthetic peptide
VARIANT                 5
                        note = M or T
source                  1..7
                        mol_type = protein
                        organism = synthetic construct
SEQUENCE: 12
GYSFXNY                                                            7

SEQ ID NO: 13           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 13
GYSFTNY                                                            7

SEQ ID NO: 14           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 14
GYSFMNY                                                            7

SEQ ID NO: 15           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 15
YPGGDY                                                             6

SEQ ID NO: 16           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 16
SGNYDEVAY                                                          9

SEQ ID NO: 17           moltype = AA  length = 975
FEATURE                 Location/Qualifiers
```

-continued

```
REGION                   1..975
                         note = Description of Artificial Sequence: Synthetic
                          polypeptide
source                   1..975
                         mol_type = protein
                         organism = synthetic construct
SEQUENCE: 17
EVQLVQSGAE VKKPGESLKI SCKGSGYSFT NYWLGWVRQM PGKGLEWMGD IYPGGDYPTY  60
SEKFKVQVTI SADKSISTAY LQWSSLKASD TAMYYCARSG NYDEVAYWGQ GTLVTVSSAS 120
TKGPSVFPLA PSSKSTSGGT AALGCLVKDY FPEPVTVSWN SGALTSGVHT FPAVLQSSGL 180
YSLSSVVTVP SSSLGTQTYI CNVNHKPSNT KVDKKVEPKS CDKTHTCPPC PAPELLGGPS 240
VFLFPPKPKD TLMISRTPEV TCVVVDVSHE DPEVKFNWYV DGVEVHNAKT KPREEQYNST 300
YRVVSVLTVL HQDWLNGKEY KCKVSNKALP APIEKTISKA KGQPREPQVY TLPPSRDELT 360
KNQVSLTCLV KGFYPSDIAV EWESNGQPEN NYKTTPPVLD SDGSFFLYSK LTVDKSRWQQ 420
GNVFSCSVMH EALHNHYTQK SLSLSPGKGS SETQANSTTD ALNVLLIIVD DLRPSLGCYG 480
DKLVRSPNID QLASHSLLFQ NAFAQQAVCA PSRVSFLTGR RPDTTRLYDF NSYWRVHAGN 540
FSTIPQYFKE NGYVTMSVGK VFHPGISSNH TDDSPYSWSF PPYHPSSEKY ENTKTCRGPD 600
GELHANLLCP VDVLDVPEGT LPDKQSTEQA IQLLEKMKTS ASPFFLAVGY HKPHIPFRYP 660
KEFQKLYPLE NITLAPDPEV PDGLPPVAYN PWMDIRQRED VQALNISVPY GPIPVDFQRK 720
IRQSYFASVS YLDTQVGRLL SALDDLQLAN STIIAFTSDH GWALGEHGEW AKYSNFDVAT 780
HVPLIFYVPG RTASLPEAGE KLFPYLDPFD SASQLMEPGR QSMDLVELVS LFPTLAGLAG 840
LQVPPRCPVP SFHVELCREG KNLLKHFRFR DLEEDPYLPG NPRELIAYSQ YPRPSDIPQW 900
NSDKPSLKDI KIMGYSIRTI DYRYTVWVGF NPDEFLANFS DIHAGELYFV DSDPLQDHNM 960
YNDSQGGDLF QLLMP                                                 975

SEQ ID NO: 18              moltype = AA  length = 975
FEATURE                    Location/Qualifiers
REGION                     1..975
                           note = Description of Artificial Sequence: Synthetic
                            polypeptide
SITE                       509
                           note = Formylglycine
source                     1..975
                           mol_type = protein
                           organism = synthetic construct
SEQUENCE: 18
EVQLVQSGAE VKKPGESLKI SCKGSGYSFT NYWLGWVRQM PGKGLEWMGD IYPGGDYPTY  60
SEKFKVQVTI SADKSISTAY LQWSSLKASD TAMYYCARSG NYDEVAYWGQ GTLVTVSSAS 120
TKGPSVFPLA PSSKSTSGGT AALGCLVKDY FPEPVTVSWN SGALTSGVHT FPAVLQSSGL 180
YSLSSVVTVP SSSLGTQTYI CNVNHKPSNT KVDKKVEPKS CDKTHTCPPC PAPELLGGPS 240
VFLFPPKPKD TLMISRTPEV TCVVVDVSHE DPEVKFNWYV DGVEVHNAKT KPREEQYNST 300
YRVVSVLTVL HQDWLNGKEY KCKVSNKALP APIEKTISKA KGQPREPQVY TLPPSRDELT 360
KNQVSLTCLV KGFYPSDIAV EWESNGQPEN NYKTTPPVLD SDGSFFLYSK LTVDKSRWQQ 420
GNVFSCSVMH EALHNHYTQK SLSLSPGKGS SETQANSTTD ALNVLLIIVD DLRPSLGCYG 480
DKLVRSPNID QLASHSLLFQ NAFAQQAVGA PSRVSFLTGR RPDTTRLYDF NSYWRVHAGN 540
FSTIPQYFKE NGYVTMSVGK VFHPGISSNH TDDSPYSWSF PPYHPSSEKY ENTKTCRGPD 600
GELHANLLCP VDVLDVPEGT LPDKQSTEQA IQLLEKMKTS ASPFFLAVGY HKPHIPFRYP 660
KEFQKLYPLE NITLAPDPEV PDGLPPVAYN PWMDIRQRED VQALNISVPY GPIPVDFQRK 720
IRQSYFASVS YLDTQVGRLL SALDDLQLAN STIIAFTSDH GWALGEHGEW AKYSNFDVAT 780
HVPLIFYVPG RTASLPEAGE KLFPYLDPFD SASQLMEPGR QSMDLVELVS LFPTLAGLAG 840
LQVPPRCPVP SFHVELCREG KNLLKHFRFR DLEEDPYLPG NPRELIAYSQ YPRPSDIPQW 900
NSDKPSLKDI KIMGYSIRTI DYRYTVWVGF NPDEFLANFS DIHAGELYFV DSDPLQDHNM 960
YNDSQGGDLF QLLMP                                                 975

SEQ ID NO: 19              moltype = AA  length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 19
GGGGS                                                            5

SEQ ID NO: 20              moltype = AA  length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 20
GGGGGS                                                           6

SEQ ID NO: 21              moltype = AA  length = 5
FEATURE                    Location/Qualifiers
REGION                     1..5
                           note = Description of Artificial Sequence: Synthetic peptide
source                     1..5
```

-continued

```
                         mol_type = protein
                         organism = synthetic construct
SEQUENCE: 21
SGGGG                                                            5

SEQ ID NO: 22           moltype =    length =
SEQUENCE: 22
000

SEQ ID NO: 23           moltype =    length =
SEQUENCE: 23
000

SEQ ID NO: 24           moltype = AA   length = 217
FEATURE                 Location/Qualifiers
source                  1..217
                        mol_type = protein
                        organism = Homo sapiens
SEQUENCE: 24
APELLGGPSV FLFPPKPKDT LMISRTPEVT CVVVDVSHED PEVKFNWYVD GVEVHNAKTK   60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESNGQPENN YKTTPPVLDS DGSFFLYSKL  180
TVDKSRWQQG NVFSCSVMHE ALHNHYTQKS LSLSPGK                          217

SEQ ID NO: 25           moltype = AA   length = 15
FEATURE                 Location/Qualifiers
source                  1..15
                        mol_type = protein
                        organism = Homo sapiens
SEQUENCE: 25
EPKSCDKTHT CPPCP                                                  15

SEQ ID NO: 26           moltype = AA   length = 760
FEATURE                 Location/Qualifiers
source                  1..760
                        mol_type = protein
                        organism = Homo sapiens
SEQUENCE: 26
MMDQARSAFS NLFGGEPLSY TRFSLARQVD GDNSHVEMKL AVDEEENADN NTKANVTKPK   60
RCSGSICYGT IAVIVFFLIG FMIGYLGYCK GVEPKTECER LAGTESPVRE EPGEDFPAAR  120
RLYWDDLKRK LSEKLDSTDF TGTIKLLNEN SYVPREAGSQ KDENLALYVE NQFREFKLSK  180
VWRDQHFVKI QVKDSAQNSV IIVDKNGRLV YLVENPGGYV AYSKAATVTG KLVHANFGTK  240
KDFEDLYTPV NGSIVIVRAG KITFAEKVAN AESLNAIGVL IYMDQTKFPI VNAELSFFGH  300
AHLGTGDPYT PGFPSFNHTQ FPPSRSSGLP NIPVQTISRA AAEKLFGNME GDCPSDWKTD  360
STCRMVTSES KNVKLTVSNV LKEIKILNIF GVIKGFVEPD HYVVVGAQRD AWGPGAAKSG  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QNVKHPVTGQ FLYQDSNWAS KVEKLTLDNA  540
AFPFLAYSGI PAVSFCFCED TDYPYLGTTM DTYKELIERI PELNKVARAA AEVAGQFVIK  600
LTHDVELNLD YERYNSQLLS FVRDLNQYRA DIKEMGLSLQ WLYSARGDFF RATSRLTTDF  660
GNAEKTDRFV MKKLNDRVMR VEYHFLSPYV SPKESPFRHV FWGSGSHTLP ALLENLKLRK  720
QNNGAFNETL FRNQLALATW TIQGAANALS GDVWDIDNEF                       760

SEQ ID NO: 27           moltype = AA   length = 181
FEATURE                 Location/Qualifiers
source                  1..181
                        mol_type = protein
                        organism = Homo sapiens
SEQUENCE: 27
NSVIIVDKNG RLVYLVENPG GYVAYSKAAT VTGKLVHANF GTKKDFEDLY TPVNGSIVIV   60
RAGKITFAEK VANAESLNAI GVLIYMDQTK FPIVNAELSF FGHAHLGTGD PYTPGFPSFN  120
HTQFPPSRSS GLPNIPVQTI SRAAAEKLFG NMEGDCPSDW KTDSTCRMVT SESKNVKLTV  180
S                                                                181
```

What is claimed is:

1. A pharmaceutical composition comprising a fusion protein and a pharmaceutically acceptable excipient, wherein the fusion protein comprises:
   (a) two light chain amino acid sequences, each consisting of SEQ ID NO: 5;
   (b) a first heavy chain amino acid sequence, a linker, and an iduronate 2-sulfatase (IDS) amino acid sequence, which together consist of SEQ ID NO:17 or SEQ ID NO: 18; and
   (c) a second heavy chain amino acid sequence, a linker, and an IDS amino acid sequence, which together consist of SEQ ID NO: 17 or SEQ ID NO:18;

and wherein the fusion protein comprises at least about 6 mol/mol sialic acid:fusion protein.

2. The pharmaceutical composition of claim 1, wherein the fusion protein comprises from about 6 to about 19 mol/mol sialic acid:fusion protein.

3. The pharmaceutical composition of claim 1, wherein the fusion protein comprises from about 6 to about 16 mol/mol sialic acid:fusion protein.

4. The pharmaceutical composition of claim 1, wherein the fusion protein comprises about 6 mol/mol sialic acid: fusion protein.

5. The pharmaceutical composition of claim 4, wherein the fusion protein comprises 6 mol/mol sialic acid:fusion protein.

6. The pharmaceutical composition of claim 1, wherein the fusion protein comprises from about 1.5 to about 2.5 mol/mol mannose-6-phosphate (M6P):fusion protein.

7. The pharmaceutical composition of claim 1, wherein the pharmaceutically acceptable excipient is selected from the group consisting of trehalose, sucrose, mannitol, polyethylene glycol, polypropylene glycol, polyethylene-polypropylene glycol, and glycine.

8. The pharmaceutical composition of claim 7, wherein the pharmaceutically acceptable excipient is polyethylene glycol, polypropylene glycol, or polyethylene-polypropylene glycol.

9. The pharmaceutical composition of claim 4, wherein the pharmaceutically acceptable excipient is selected from the group consisting of trehalose, sucrose, mannitol, polyethylene glycol, polypropylene glycol, polyethylene-polypropylene glycol, and glycine.

10. The pharmaceutical composition of claim 9, wherein the pharmaceutically acceptable excipient is polyethylene glycol, polypropylene glycol, or polyethylene-polypropylene glycol.

11. The pharmaceutical composition of claim 5, wherein the pharmaceutically acceptable excipient is selected from the group consisting of trehalose, sucrose, mannitol, polyethylene glycol, polypropylene glycol, polyethylene-polypropylene glycol, and glycine.

12. The pharmaceutical composition of claim 11, wherein the pharmaceutically acceptable excipient is polyethylene glycol, polypropylene glycol, or polyethylene-polypropylene glycol.

13. A fusion protein comprising:
(a) two light chain amino acid sequences, each consisting of SEQ ID NO: 5;
(b) a first heavy chain amino acid sequence, a linker, and an iduronate 2-sulfatase (IDS) amino acid sequence, which together consist of SEQ ID NO: 18; and
(c) a second heavy chain amino acid sequence, a linker, and an IDS amino acid sequence, which together consist of SEQ ID NO: 18;
wherein the fusion protein comprises at least about 6 mol/mol sialic acid:fusion protein.

14. The fusion protein of claim 13, wherein the fusion protein comprises from about 6 to about 19 mol/mol sialic acid:fusion protein.

15. The fusion protein of claim 13, wherein the fusion protein comprises from about 6 to about 16 mol/mol sialic acid:fusion protein.

16. The fusion protein of claim 13, wherein the fusion protein comprises about 6 mol/mol sialic acid:fusion protein.

17. The fusion protein of claim 16, wherein the fusion protein comprises 6 mol/mol sialic acid:fusion protein.

18. The fusion protein of claim 13, wherein the fusion protein comprises from about 1.5 to about 2.5 mol/mol mannose-6-phosphate (M6P):fusion protein.

19. The pharmaceutical composition of claim 1, wherein the fusion protein comprises:
(a) two light chain amino acid sequences, each consisting of SEQ ID NO: 5;
(b) a first heavy chain amino acid sequence, a linker, and an IDS amino acid sequence, which together consist of SEQ ID NO: 18; and
(c) a second heavy chain amino acid sequence, a linker, and an IDS amino acid sequence, which together consist of SEQ ID NO:18.

* * * * *